(12) United States Patent
Wong

(10) Patent No.: US 9,408,635 B2
(45) Date of Patent: Aug. 9, 2016

(54) EXTERNAL FIXATION

(71) Applicant: Wright Medical Technology, Inc., Memphis, TN (US)

(72) Inventor: Kian-Ming (Kevin) Wong, Lakeland, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 84 days.

(21) Appl. No.: 14/030,311

(22) Filed: Sep. 18, 2013

(65) Prior Publication Data
US 2014/0276818 A1 Sep. 18, 2014

Related U.S. Application Data

(60) Provisional application No. 61/793,165, filed on Mar. 15, 2013.

(51) Int. Cl.
*A61B 17/60* (2006.01)
*A61B 17/64* (2006.01)

(52) U.S. Cl.
CPC .......... *A61B 17/6466* (2013.01); *A61B 17/645* (2013.01)

(58) Field of Classification Search
CPC .......... A61B 17/6416; A61B 17/6458; A61B 17/6466; A61B 17/6475; A61B 17/6441; A61B 17/6425; A61B 17/645; A61B 17/6483; A61B 17/6491
See application file for complete search history.

(56) References Cited

U.S. PATENT DOCUMENTS

| | | |
|---|---|---|
| 4,365,624 A | 12/1982 | Jaquet |
| 4,393,868 A | 7/1983 | Teague |
| 4,604,997 A | 8/1986 | De Bastiani et al. |
| 4,611,586 A | 9/1986 | Agee et al. |
| 4,620,533 A | 11/1986 | Mears |

(Continued)

FOREIGN PATENT DOCUMENTS

| | | |
|---|---|---|
| WO | WO-85/03449 | 8/1985 |
| WO | WO-98/12975 | 4/1998 |

OTHER PUBLICATIONS

Department of Health & Human Services, R & R External Fixation System, "Single/multiple component metallic bone fixation appliances and accessories", Sep. 6, 2005, 2 pages.

(Continued)

*Primary Examiner* — Eduardo C Robert
*Assistant Examiner* — Julianna N Harvey
(74) *Attorney, Agent, or Firm* — Duane Morris LLP

(57) ABSTRACT

The present invention discloses an orthopedic external fixation device, an orthopedic external fixation system, and method of assembling the orthopedic external fixation device. The orthopedic external fixation device may include first and second jaws each including respective arms, a floating circular jaw disposed between the first and second jaws and defining first and second channels with the first and second jaws respectively, a plurality of pins and biasing members configured to distance the circular jaw from the first and second jaws, and a locking assembly. The first and second channels may each be configured to receive one of an embedding member or a bar of the external fixation system. The locking assembly may be at least partially received within apertures defined by the first, second, and circular jaws and may be configured to lock the first, second, and circular jaws.

17 Claims, 21 Drawing Sheets

(56) References Cited

U.S. PATENT DOCUMENTS

| | | | |
|---|---|---|---|
| 4,628,919 A | 12/1986 | Clyburn | |
| 4,895,141 A | 1/1990 | Koeneman et al. | |
| 4,920,959 A | 5/1990 | Witzel et al. | |
| 4,922,896 A | 5/1990 | Agee et al. | |
| 4,978,347 A | 12/1990 | Ilizarov et al. | |
| 5,067,954 A | 11/1991 | Ilizarov | |
| 5,108,394 A | 4/1992 | Kurokawa et al. | |
| 5,320,622 A | 6/1994 | Faccioli et al. | |
| 5,397,322 A | 3/1995 | Campopiano | |
| 5,437,666 A | 8/1995 | Tepic et al. | |
| 5,437,667 A | 8/1995 | Papierski et al. | |
| 5,443,464 A | 8/1995 | Russell et al. | |
| 5,527,309 A | 6/1996 | Shelton | |
| 5,540,686 A | 7/1996 | Zippel et al. | |
| 5,571,103 A | 11/1996 | Bailey | |
| 5,591,169 A | 1/1997 | Benoist | |
| 5,658,283 A | 8/1997 | Huebner | |
| 5,662,649 A | 9/1997 | Huebner | |
| 5,683,389 A | 11/1997 | Orsak | |
| 5,741,251 A | 4/1998 | Benoist | |
| 5,743,898 A | 4/1998 | Bailey et al. | |
| 5,752,954 A | 5/1998 | Mata et al. | |
| 5,810,814 A | 9/1998 | Newson | |
| 5,891,144 A | 4/1999 | Mata et al. | |
| 5,928,230 A | 7/1999 | Tosic | |
| 5,941,879 A | 8/1999 | Walulik et al. | |
| 5,976,133 A | 11/1999 | Kraus et al. | |
| 6,001,097 A | 12/1999 | Campopiano et al. | |
| 6,053,915 A | 4/2000 | Bruchmann | |
| 6,283,964 B1 | 9/2001 | Weiner | |
| 6,328,737 B1 | 12/2001 | Moorcroft et al. | |
| 6,428,540 B1 | 8/2002 | Claes et al. | |
| 6,527,775 B1 | 3/2003 | Warburton | |
| 6,629,976 B1 | 10/2003 | Gnos et al. | |
| 6,716,212 B1 | 4/2004 | Pickens | |
| 6,793,655 B2 | 9/2004 | Orsak | |
| 6,866,665 B2 | 3/2005 | Orbay | |
| 7,291,148 B2 | 11/2007 | Agee et al. | |
| 8,277,448 B2 | 10/2012 | Daluiski et al. | |
| 2003/0109879 A1 | 6/2003 | Orsak | |
| 2003/0149429 A1 | 8/2003 | Ferrante et al. | |
| 2004/0133200 A1 | 7/2004 | Ruch et al. | |
| 2005/0043730 A1 | 2/2005 | Janowski et al. | |
| 2006/0235383 A1 | 10/2006 | Hollawell | |
| 2006/0255521 A1* | 11/2006 | Brunner et al. | 269/86 |
| 2007/0055234 A1 | 3/2007 | McGrath et al. | |
| 2008/0221571 A1 | 9/2008 | Daluiski et al. | |
| 2009/0024128 A1 | 1/2009 | Nakamura et al. | |
| 2009/0088751 A1* | 4/2009 | Mullaney | 606/59 |
| 2010/0298827 A1* | 11/2010 | Cremer et al. | 606/54 |
| 2011/0066151 A1* | 3/2011 | Murner et al. | 606/54 |
| 2012/0150185 A1* | 6/2012 | Mullaney | 606/59 |

OTHER PUBLICATIONS

Division of General, Restorative, and Neurological Devices, Indications for Use, 510(k) Summary R & R External Fixator System, Jul. 20, 2005, 4 pages.

FDA>CDHR>510(k) Premarket Notification Database Search, http://www.accessdata.fda.gov/scripts/cdrh/cfdocs/cfPMN/pmn.cfm?ID=86480, 510(k) Premarket Notification Database, Jun. 30, 2005, 3 pages.

EBI-Products, http://www.ebimedical.com/products/detail.cfm?p=090607, MiniFixator and MiniLengthener, Jul. 18, 2005, 4 pages.

Acumed—Small Bone External Fixation System, http://www.acumed.net/product-detail.php?productID=35, Jul. 18, 2005, 4 pages.

International Search Report for PCT/US2008/056001.

Written Opinion for PCT/US2008/056001.

Gradl, et al.; "Fractures of the Distal Radius Treated With a Nonbridging External Fixation Technique Using Multiplanar K-Wires"; The Journal of Hand Surgery; 2005; 30A: pp. 960-968.

Synthes (USA), "External Fixation" (2000).

Nakamura, Kozo, External Wound Fixation Device, Aug. 9, 2006, WIPO, WO 2006/092863 A1, all pages.

* cited by examiner

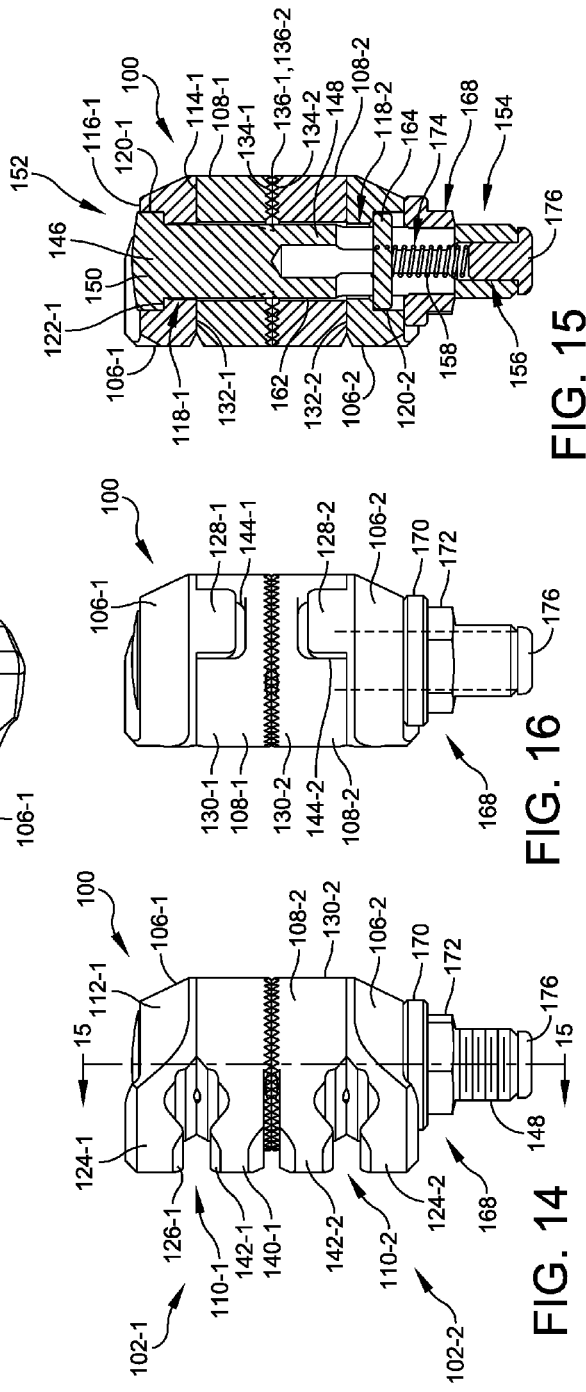
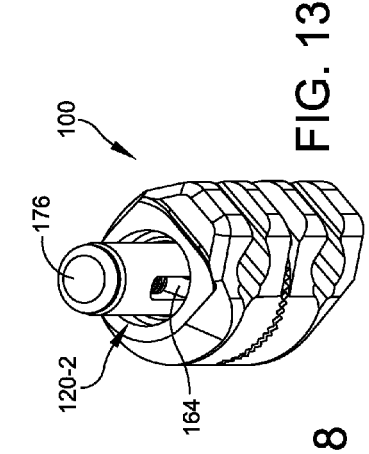
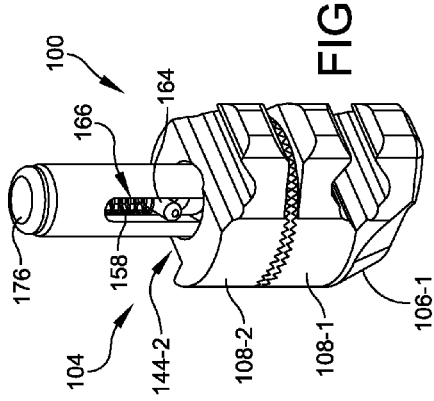
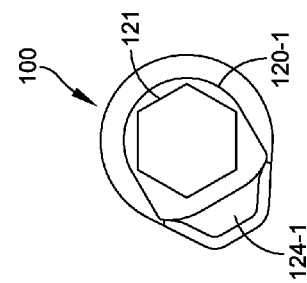

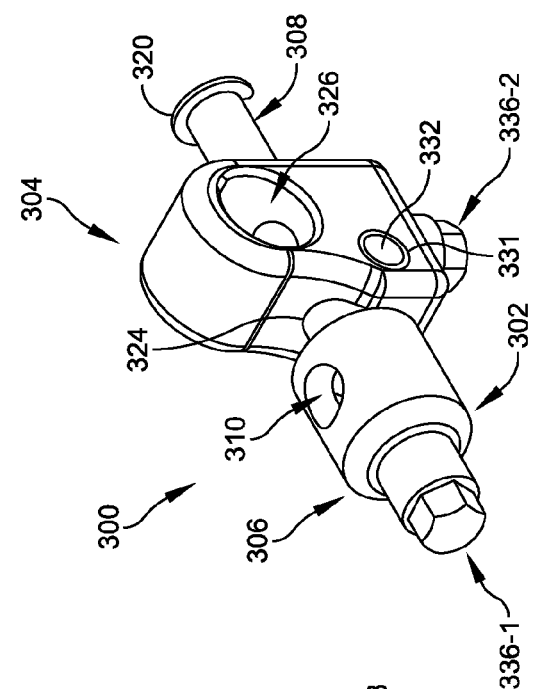
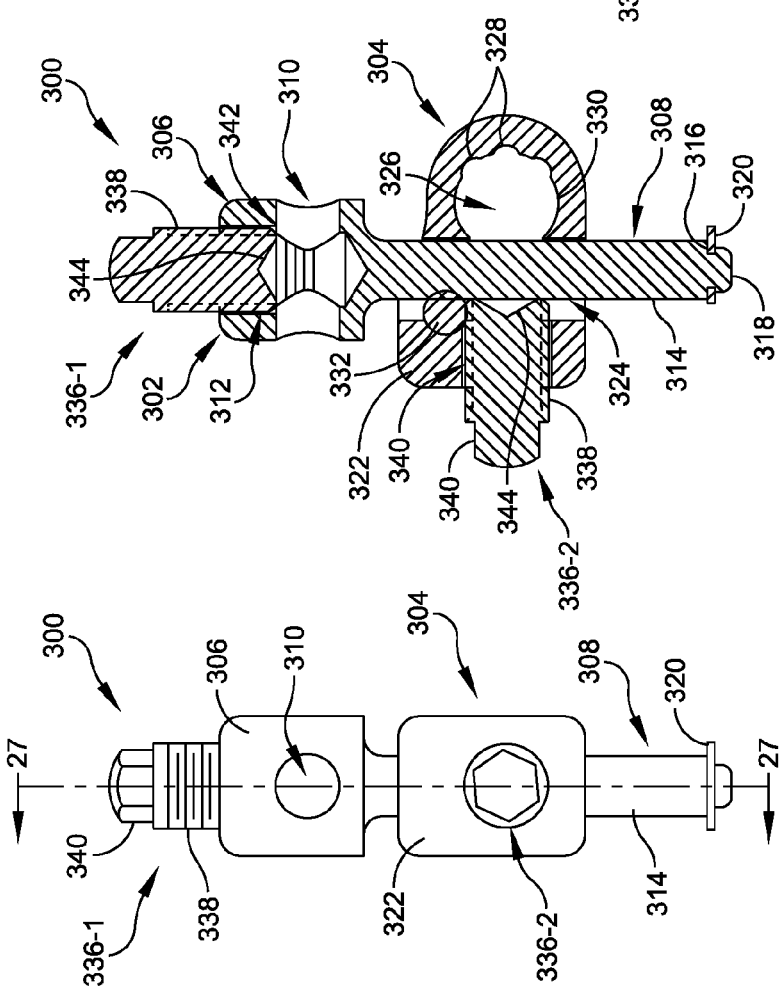

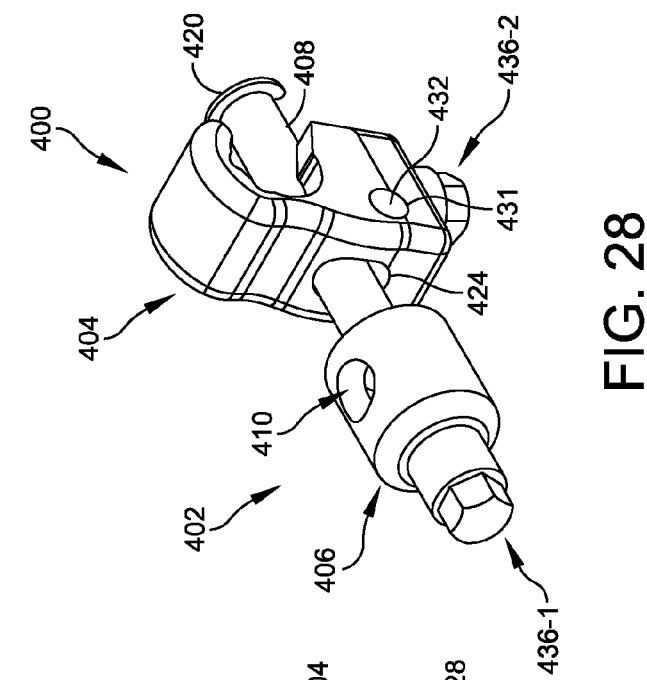
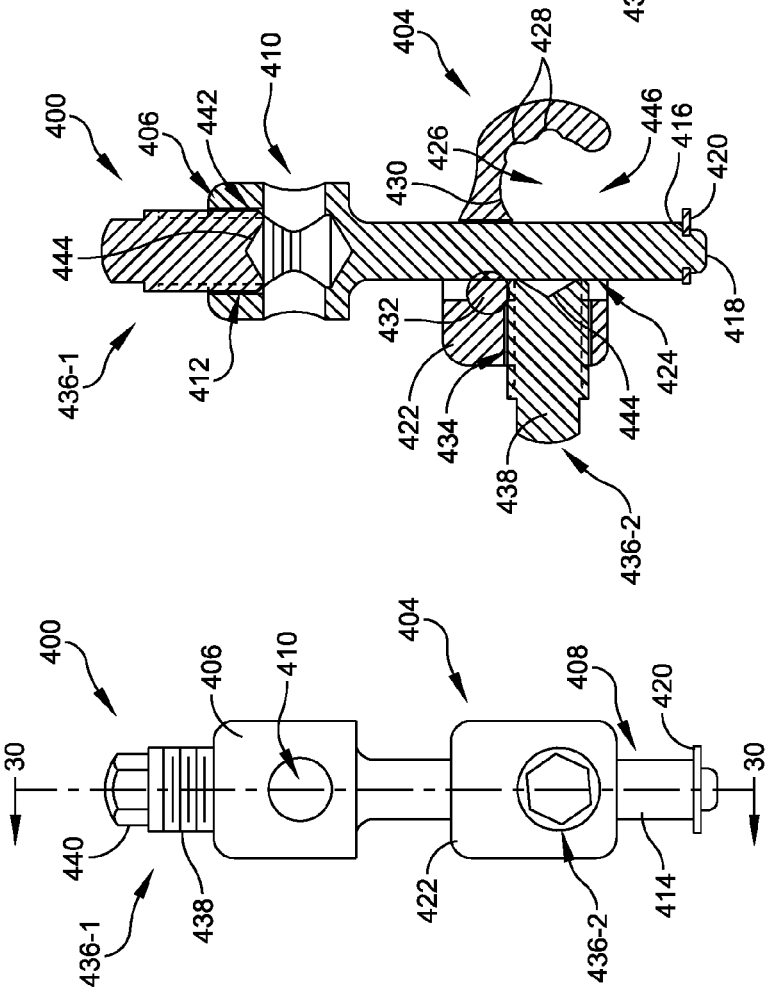

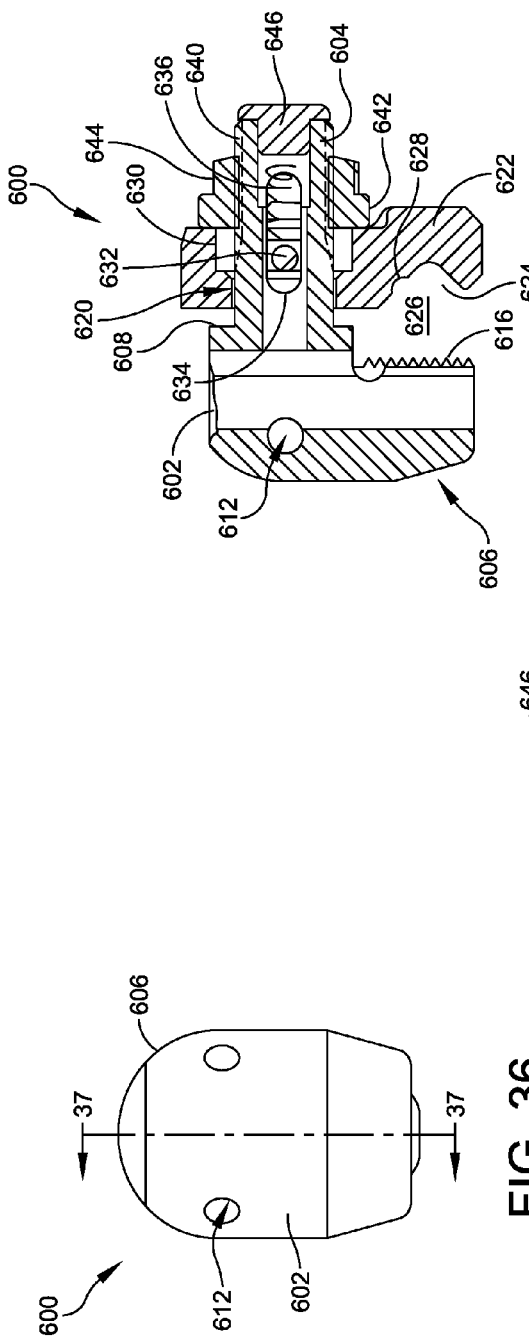

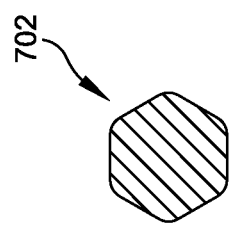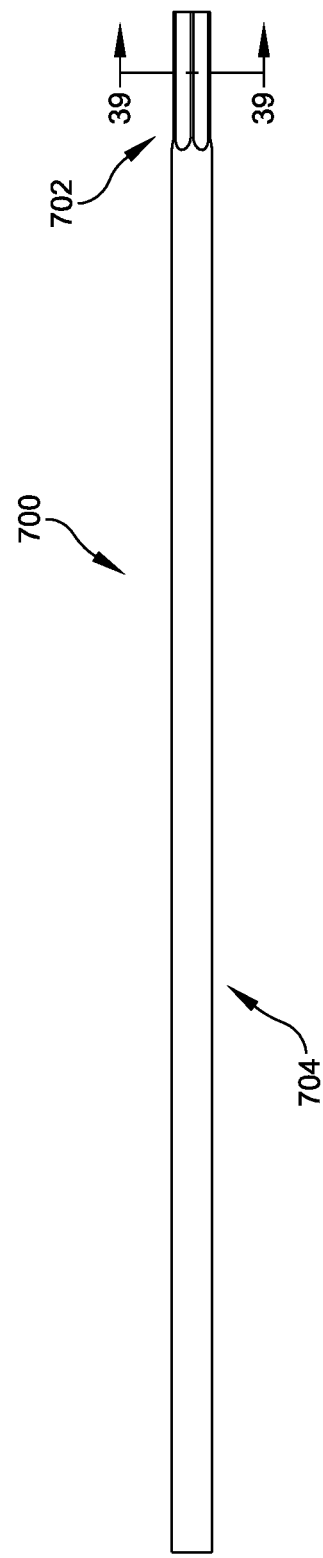

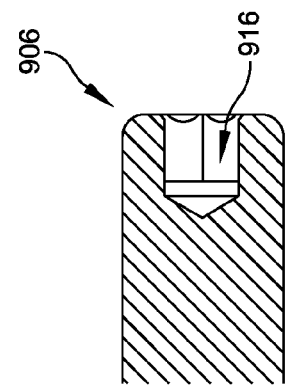
FIG. 47
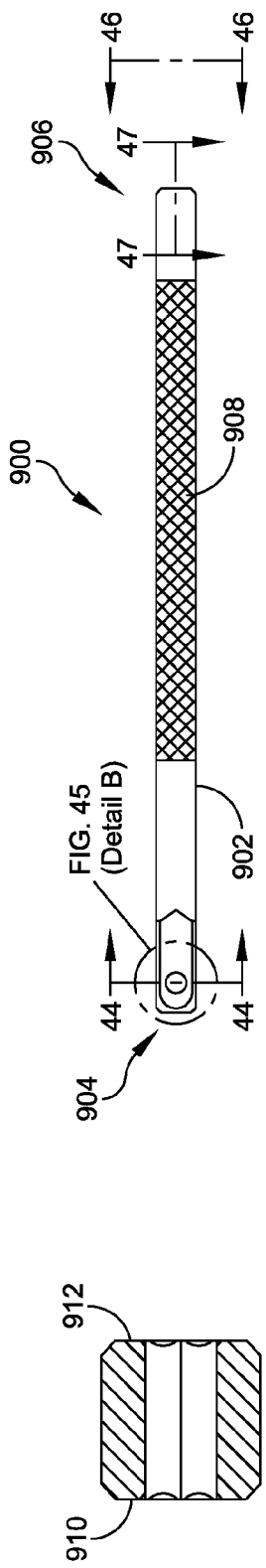
FIG. 43
FIG. 46
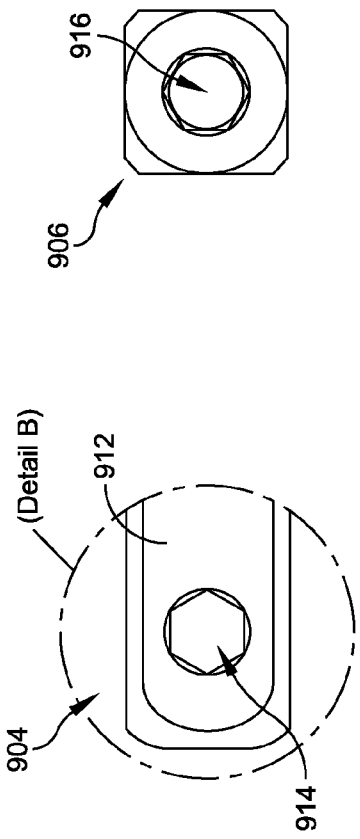
FIG. 45
FIG. 44

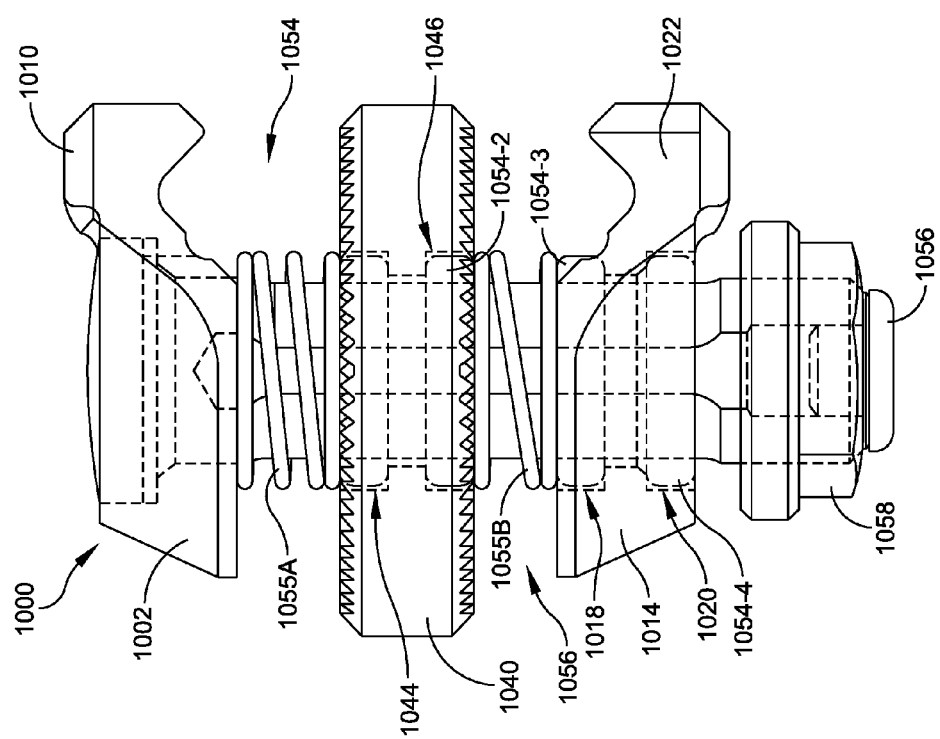

EXTERNAL FIXATION

CROSS-REFERENCE TO RELATED APPLICATIONS

This application also claims priority to U.S. Provisional Patent Application No. 61/793,165, filed on Mar. 15, 2013, the entirety of which is herein incorporated by reference.

SUMMARY

In some embodiments, an orthopedic external fixation device includes first and second jaws each including respective arms. A floating circular jaw is disposed between the first and second jaws and defines first and second channels with the first and second jaws, respectively. A plurality of pins and biasing members are configured to distance the circular jaw from the first and second jaws. The first and second channels may each be configured to receive one of an embedding member or a bar of an external fixation system. A locking assembly is at least partially received within apertures defined by the first, second, and circular jaws and is configured to lock the first, second, and circular jaws.

In some embodiments, an orthopedic external fixation system includes at least one bar, at least one embedding member attachable to the bar and sized and shaped for embedding in bone, and at least one embedding member connector configured to be coupled to the bar. The at least one embedding member connector includes first and second jaws each including respective arms. A floating circular jaw is disposed between the first and second jaws and defines first and second channels with the first and second jaws, respectively. A plurality of pins and biasing members are configured to distance the circular jaw from the first and second jaws. The first and second channels each are configured to receive at least one of the at least one bar and the at least one embedding member of the external fixation system. A locking assembly is at least partially received within apertures defined by the first, second, and circular jaws and is configured to lock the first, second, and circular jaws.

In some embodiments, a method of assembling an orthopedic fixation device includes sliding a first jaw onto a bolt, sliding a floating circular jaw onto said bolt, sliding a second jaw onto the bolt, inserting a plurality of pins and biasing members into an opening defined by the bolt to distance the circular jaw from the first and second jaws, and affixing a locking bolt onto a threaded portion of the bolt to secure the plurality of pins and biasing members within said opening. The circular jaw defines first and second channels with the first and second jaws, respectively, that are configured to receive at least one of an embedding member or a bar therein.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIG. 13 illustrates a bottom isometric view of an improved connector for external fixation;

FIG. 14 is a side view of the improved connector illustrated in FIG. 13;

FIG. 15 is a sectional view of the improved connector illustrated in FIG. 13 taken along line A-A in FIG. 14;

FIG. 16 is another side view of the improved connector illustrated in FIG. 13;

FIG. 17 is a top side view of the improved connector illustrated in FIG. 13;

FIG. 18 is another isometric view of the improved connector illustrated in FIG. 13 with a jaw having been removed;

FIG. 25 is an isometric view of another example of an improved connector for providing external fixation;

FIG. 26 is a bottom side view of the improved connector illustrated in FIG. 25;

FIG. 27 is a sectional view of the improved connector illustrated in FIG. 25 taken along line A-A in FIG. 26;

FIG. 28 is an isometric view of another example of an improved connector for providing external fixation;

FIG. 29 is a bottom side view of the improved connector illustrated in FIG. 28;

FIG. 30 is a sectional view of the improved connector illustrated in FIG. 28 taken along line A-A in FIG. 29;

FIG. 35 is an isometric view of another example of an improved connector for providing external fixation.

FIG. 36 is a bottom side view of the connector illustrated in FIG. 35.

FIG. 37 is a sectional view of the connector illustrated in FIG. 35 taken along line A-A in FIG. FIG. 35.

FIG. 38 is a plan view of one example of a pin including two different cross-sectional geometries in accordance with some embodiments.

FIG. 39 is sectional view of the pin illustrated in FIG. 38 taken along line A-A in FIG. 38.

FIG. 43 is a plan view of one example of a wrench in accordance with some embodiments.

FIG. 44 is a sectional view of the wrench illustrated in FIG. 43 taken along line A-A in FIG. 43.

FIG. 45 is a detail view of a portion of the wrench illustrated in FIG. 43.

FIG. 46 is a sectional view of the wrench illustrated in FIG. 43 taken along line C-C in FIG. 43.

FIG. 47 is a sectional view of the wrench illustrated in FIG. 43 taken along line D-D in FIG. 43.

FIG. 52 is another side view of the connector illustrated in FIG. 48.

DETAILED DESCRIPTION

Figure 1:
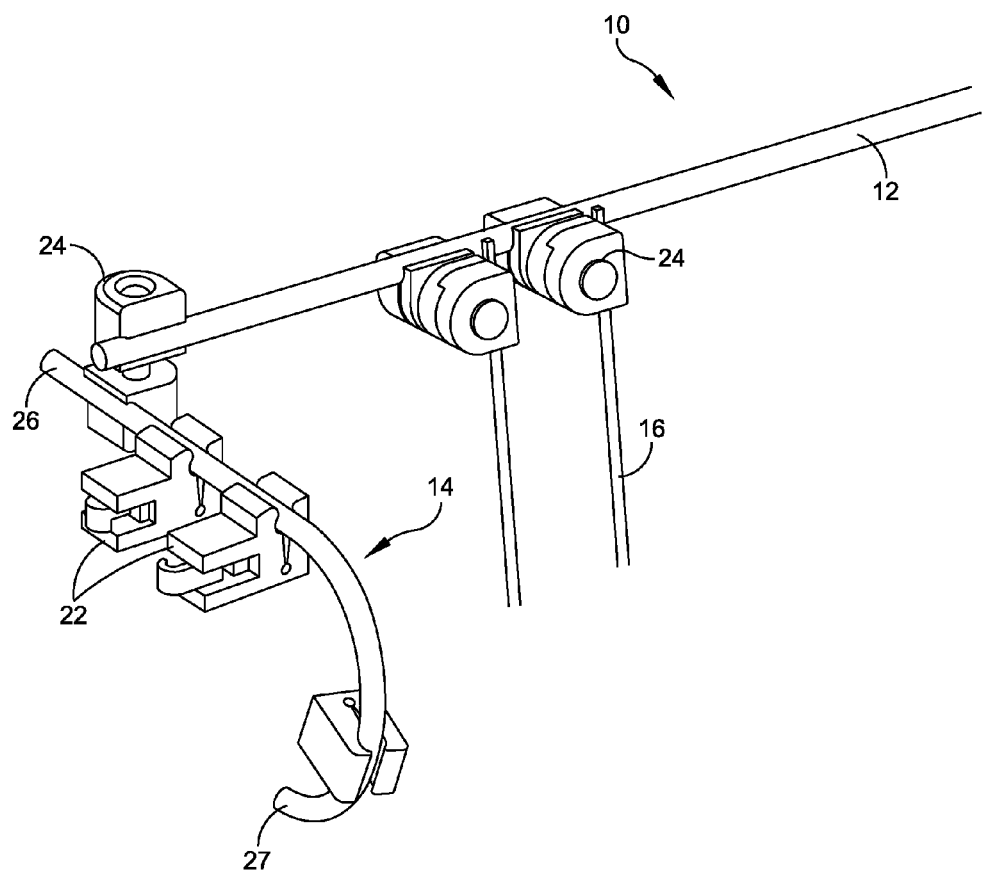
FIG. 1 depicts a perspective view of an embodiment of an external fixation system.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

An external fixation system is used to stabilize, compress, and distract fractured bone fragments in a relative alignment that facilitates bone healing. An external fixation system typically includes a number of pins, wires, and/or screws percutaneously inserted into bone fragments and clamped to one or more anchoring bars or rods. In the case of non-bridging external fixation of a distal radius fracture, a proximal bar may be fixed to the radius proximal to the fracture by threaded pins or screws, and a distal bar may be fixed to one or more fragments of the radius, distal to the fracture, by K-wires. The distal bar, or a portion thereof, may be curved, as described in more detail below. Fracture stability is achieved by insertion of K-wires, along one or more planes, into the distal bone fragment(s) and attaching the K-wires to the distal bar. The distal bar is connected to the proximal bar.

FIG. 1 shows a perspective view of an external fixation system 10 having a distal bar 14, an uncurved proximal bar 12, and a plurality of proximal embedding members 16 ("proximal pins") and proximal embedding member connectors 24. A plurality of the proximal pins 16 may be fixed to the arm of a patient and connected to the proximal bar 12 to serve as an anchor for the external fixation system 10. The proximal embedding member connectors 24 may be positioned along the length of the uncurved proximal bar 12 to anchor the proximal pins 16 appropriately. The proximal bar may optionally have detents or other surface features that mate with a proximal embedding member to define preferred connection positions. The proximal embedding member connectors 24 can be clamped at various positions along the length of the proximal pin 16.

A plurality of proximal embedding members 16 may be attachable to the proximal bar 12 directly or indirectly. Direct attachment between the proximal embedding member and the proximal bar may involve the two components making contact with one another. For example, a proximal bar may have holes sized and shaped to receive a proximal embedding member by press-fit. Holes in the proximal bar may be threaded to receive complementary threads on proximal embedding members. Direct attachment may also be accomplished by the proximal bar having a built-in clamp or other mechanisms to connect the proximal embedding member to the proximal bar without the need for an intermediate component. A proximal embedding member may also be glued to a proximal bar for direct attachment.

Indirect attachment between the proximal embedding member 16 and the proximal bar 12 may include an intermediate clamp to which both components are connected. For example, FIG. 1 shows a plurality of a proximal embedding member connectors 24 connecting a proximal embedding members to a proximal bar.

Distal embedding members 23 may be attachable to a distal bar 14 directly or indirectly in the various ways described above for proximal embedding members and a proximal bar.

The proximal bar may be fixed relative to the patient's forearm by attaching it to the radius with at least two pins/screws, typically positioned at least several centimeters apart from one another along the length of the proximal bar. When so attached, the proximal bar is typically oriented so that it runs parallel to the shaft of the radius, with respect to both the pitch of the bar and its medial/lateral skew with respect to the shaft of the radius, but nonparallel orientations, in pitch and/or skew, are also possible.

A proximal embedding member connector 24 may also connect the distal bar 14 to the uncurved proximal bar 12. FIG. 1 is an illustration of one possible attachment point between the distal bar 14 and the proximal uncurved bar 12. The distal bar 14 may be attached at different points along the length of the proximal uncurved bar 12.

The distal bar 14 has an uncurved portion 26 and a curved portion 27 and lies in a plane transverse (such as perpendicular or oblique) to the proximal bar. The curved portion may curve in a plane transverse to the proximal bar. A plurality of distal embedding member connectors 22 may connect and fix distal embedding members (such as K-wires, not shown) to the distal bar. Proximal and distal embedding members may include radiolucent features to facilitate radiographic confirmation of proper placement of wires.

The proximal and distal bars may have a variety of shapes and sizes. It may have a circular cross-section, round cross-section, elliptical cross-section, polygonal cross-section, and/or square cross-section. If the cross-section has flat sides, the edges defining the sides may be rounded. A bar may have a diameter in the range of about 1 mm to about 12 mm, about 3 mm to about 11 mm, about 3 mm, about 4 mm, about 5 mm, about 8 mm, and/or about 11 mm. The diameter of a bar may be constant along the length of the bar or may vary. (If the bar has other than a circular cross-section, the "diameter" refers to the longest segment that can be obtained by joining two points at the edge of the cross-section.) A bar may be solid or hollow inside. A bar may have a length in the range of about 3 cm to about 30 cm.

The proximal and distal bars may be made of a wide variety of materials. The bars may be made, in whole or in part, from carbon fiber reinforced composite, metal, stainless steel, titanium, aluminum (such as grades 6061 and 7075), plastic, polysulfone, polyether sulfone (such as RADEL®-A plastic resin), polyphenylsulfone (such as RADEL®-R plastic resin), PEEK, and carbon filled materials, among others. A bar may be radiolucent. A bar may be of unitary construction (i.e., is formed from a single piece of material, without any joints or connections) or may be formed by joining two or more pieces together.

The length of the uncurved portion 26 of the distal bar may be in the range of about 4 centimeters to about 6 centimeters. The curved portion 27 of the distal bar may curve through an arc of less than 45 degrees, at least 45 degrees, at least 60 degrees, at least 90 degrees, between about 90 degrees and about 180 degrees, about 180 degrees, and/or at least 180 degrees. The curved portion 27 of the distal bar 14 may have a constant curvature or a non-constant curvature. A non-constant curvature may follow a sector of, for example, a noncircular ellipse, a hyperellipse, a hypoellipse, an oval, a parabola, a hyperbola, or an involute, among other shapes. The distal bar 14 may have a first portion having a first curvature and a second portion having a second curvature which is different from the first curvature.

One or more curved portions of the distal bar 14 may follow a sector of a circle. The distal bar 14 may curve through at least ⅛ of the circumference of a circle, at least ⅙ of the circumference of a circle, at least ¼ of the circumference of a circle, between ¼ and ½ of the circumference of a circle, about ½ of the circumference of a circle, and/or at least ½ of the circumference of a circle. The circle that the distal bar curved portion follows may have a radius in the range of about 0.5 inches to about 5 inches, about 1 inch to about 2 inches, about 1 inch, exactly 1 inch, about 1.5 inches, exactly 1.5 inches, about 2 inches, and/or exactly 2 inches.

One or more curved portions of the distal bar 14 may follow the curvature of a non-circular ellipse. The distal bar 14 may follow the curvature of an ellipse having a major axis of about 7 cm in length and a minor axis of about 5 cm in length. The distal bar 14 may follow the curvature of an ellipse having a major axis of about 6 cm in length and a minor axis of about 4 cm in length. Alternatively, the distal bar 14 may follow the curvature of an ellipse having an eccentricity in the range of about 0.5 to about 0.8, about 0.6 to about 0.8, and/or about 0.69 to about 0.75. (Eccentricity of an ellipse is an unitless quantity that indicates deviation from a circular shape and is defined to equal $\sqrt{1-(b^2/a^2)}$, where a and b are the major and minor axes, respectively, of the ellipse. A circle has an eccentricity of zero and a noncircular ellipse has an eccentricity that is greater than zero but less than one. The eccentricity of an ellipse that reasonably approximates the cross-section of a human wrist typically falls in the range of about 0.6 to about 0.8. The eccentricity of an ellipse that reasonably approximates the cross-section of a human finger typically falls in the range of about 0.5 to about 0.6. The distal bar 14 may curve through at least ⅛ of the circumference of an ellipse, at least ⅙ of the circumference of an ellipse, at least ¼ of the circumference of an ellipse, between ¼ and ½ of the circumference of an ellipse, about ½ of the circumference of an ellipse, and/or at least ½ of the circumference of an ellipse.

The distal bar 14 may be positioned on the skin or with space between it and the patient's skin to allow for postoperative swelling. The distal bar may be spaced apart from the skin at distance in the range of 0 cm to about 3 cm, 0 cm to about 2 cm, 0 cm to about 1.5 cm, about 1 cm to about 1.5 cm, and/or about 0.5 cm to 1.5 cm. For example, the distal bar may be designed to follow a curve appropriately larger than the relevant portion of the patient's anatomy. If no swelling is expected, then a bar that contacts or lies within a few millimeters of the skin may be used to provide a low-profile fixation system.

Figure 2:
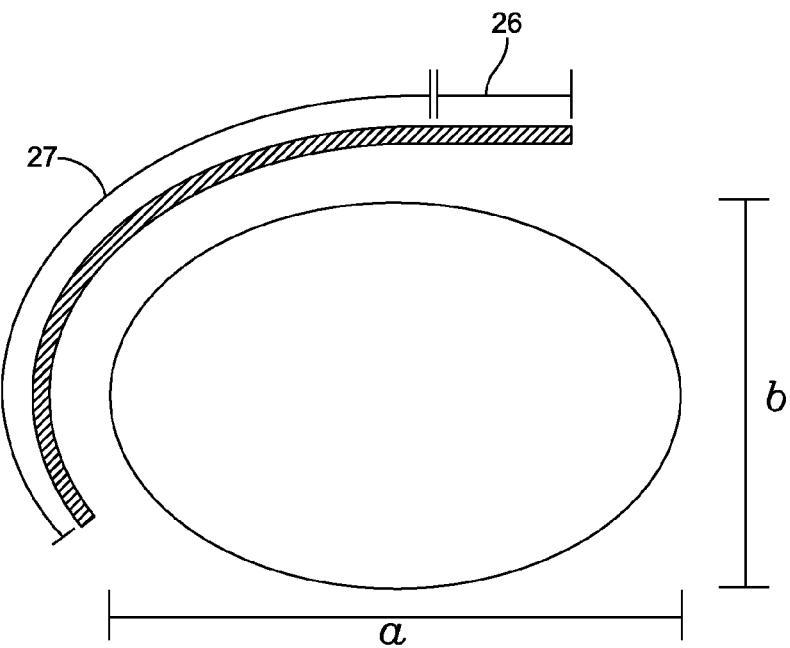
FIG. 2 shows an embodiment of a distal bar having an uncurved portion and a curved portion following the curvature of a noncircular ellipse.

FIG. 2 shows an embodiment of a distal bar. In the depicted embodiment, the distal bar 14 has a curved portion 27 and an uncurved portion 26. The curved portion extends from one end of the uncurved portion and follows an elliptical curve through somewhat more than ¼ of the circumference of the ellipse. The ellipse that the curved portion follows has major and minor axes that exceed the major and minor axes, a and b, respectively, of the depicted ellipse that approximates the cross-section of the anatomy about which the bar is positioned (such as the forearm in the vicinity of the distal radius).

Figure 3:
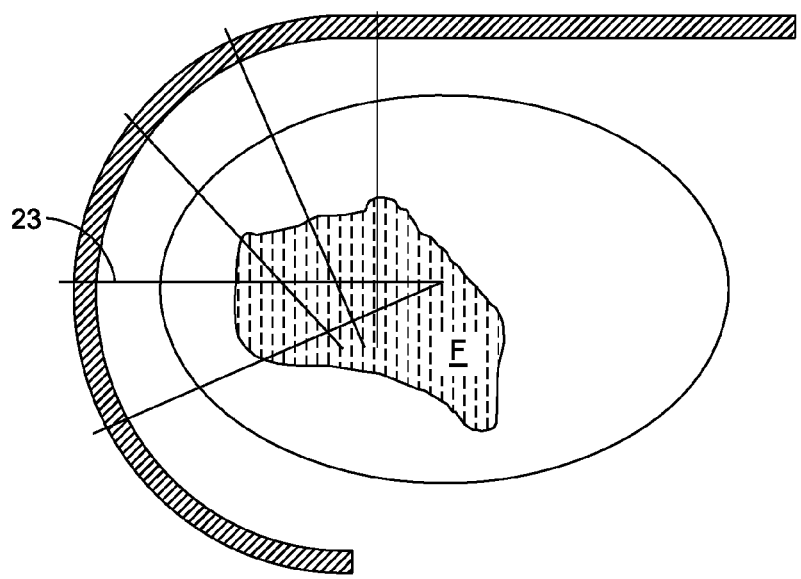
FIG. 3 shows an embodiment of a distal bar having an uncurved portion and a semicircular curved portion, with a plurality of distal embedding members extending from the distal bar into bone.

FIG. 3 depicts another embodiment of a distal bar. In this embodiment, the curved portion has a constant curvature (i.e., it is circular) and curves through an arc of 180 degrees (i.e., it has a semicircular shape). This distal bar is referred to herein as a "J-bar" in view of its shape. FIG. 3 also depicts an exemplary use of the distal bar. Each of a plurality of distal embedding members 23 (such as K-wires) extend from the distal bar into a bone fragment F. The distal embedding members may be so oriented and positioned relative to one another that they form a "subchondral scaffold" of wires that support the fragment in one or more planes. The distal embedding members may also be oriented to cross the fracture lines.

Figure 4:
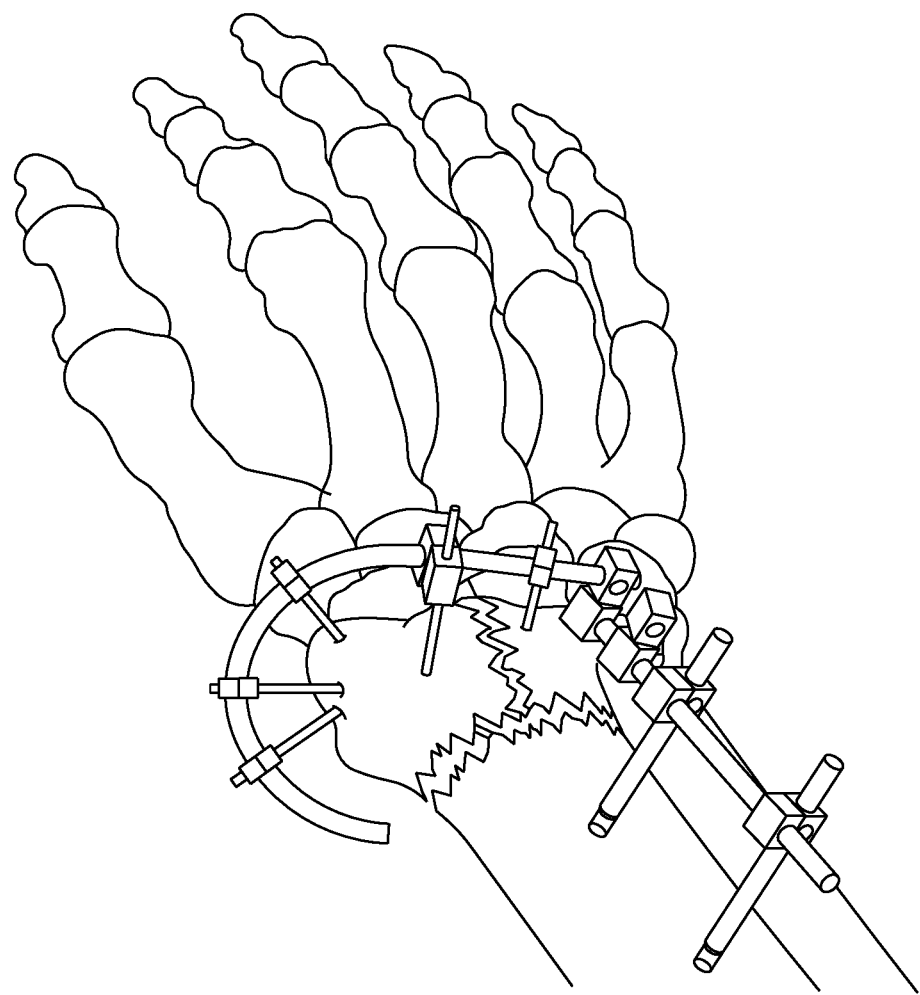
FIG. 4 shows an exemplary use of an embodiment illustrated in FIG. 1 with a plurality of distal embedding members extending from the distal bar into bone.

In one exemplary use shown in FIG. 4, the system is used in the repair of a distal radius fracture. In such a scenario, the curved portion 27 of the distal bar 14 may be sized and shaped so that it wraps around the patient's distal forearm on the radial (anatomically lateral) side. The proximal bar is fixed to the shaft of the radius with pins and connectors. The distal bar is fixed to the proximal bar by a connector. A plurality of K-wires are fixed to the distal bar by connectors and embedded in the distal radius fragments. The curved portion of the distal bar permits placement of the K-wires at a wide variety of angles from several positions around the distal radius without the need to bend or otherwise distort the wires. The system is flexible in that the users can bend the wires toward the bars as long as the section of the wire to which the clamp will be attached is straight. Using unbent K-wires helps minimize wobble, shift, torque, and shear stress, and to fit between the wires and clamps. The K-wires may, however, be bent and still provide enough support if proper placement into the distal fragment requires it.

Figure 5:
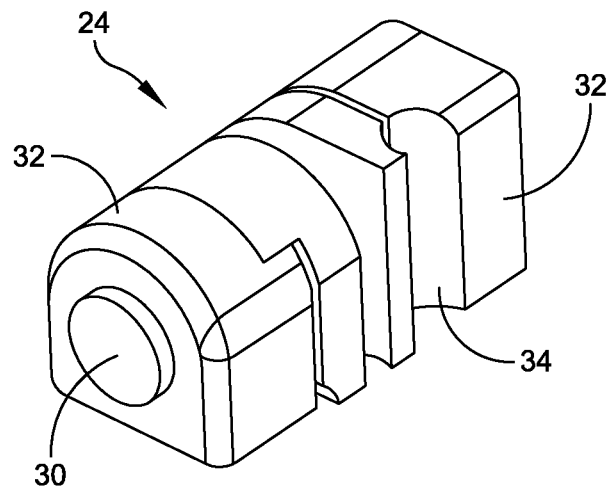
FIGS. 5-6 respectively show perspective and side views of a proximal embedding member connector.
Figure 6:
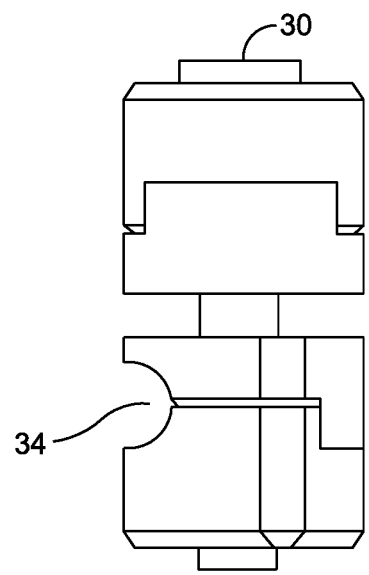

FIGS. 5 and 6 illustrate an embodiment of a proximal embedding member connector 24 having two grooved blocks 32. The blocks may be identical to one another. The block defines a groove having a semicircular shape-shaped groove. In the depicted embodiment, the blocks define semicircular grooves 34 that are oriented perpendicular to one another. The two blocks 32 may be oriented at other angles with respect to each other, so that the grooves 34 may be oriented in a wide range of angles depending on a patient's need. The grooves may be sized and shaped to receive the uncurved proximal bar 12 and/or the proximal pins 16. Once a desired position of the proximal embedding member connectors 24 is obtained, a locking screw 30 may simultaneously lock the two blocks 32 having semicircular grooves 34 to each other and fix the locked blocks to the uncurved proximal bar 12 as shown in FIG. 1. By tightening the screw, the clamping force is applied and two blocks 32 will come together until they contact one another. FIG. 6 represents an embodiment of an unlocked configuration of a proximal embedding member connector 24.

Figure 9:
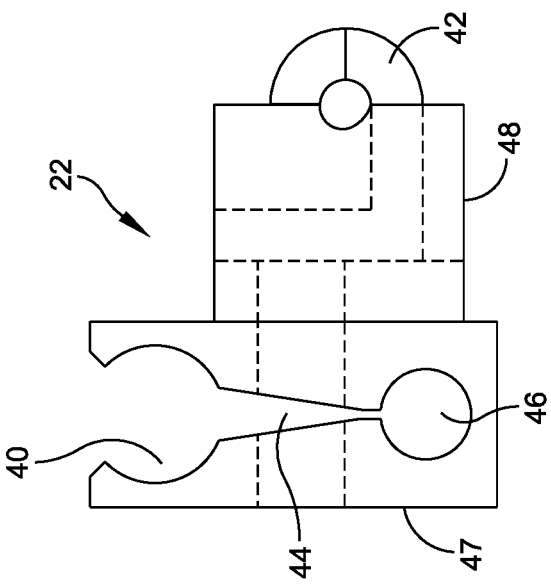
FIGS. 7-9 respectively illustrate perspective, unlocked front, and locked front views of a distal embedding member connector.
Figure 8:
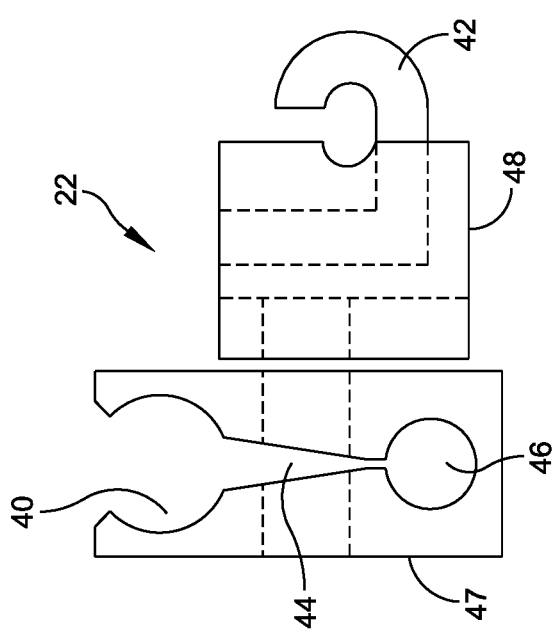
Figure 7:
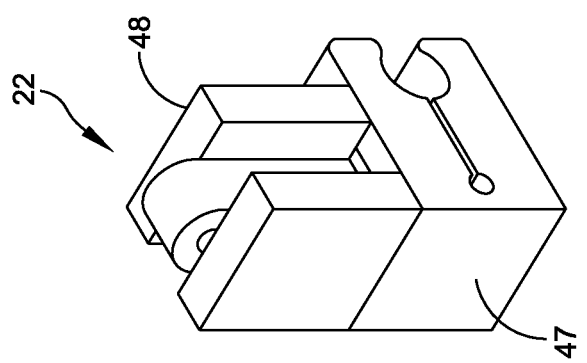

FIGS. 7-9 show various views of an exemplary embodiment of a distal embedding member connector 22. The depicted embodiment includes a block 47 and a block 48, each having a groove to receive a distal bar 14 and a distal embedding member 20, respectively. FIG. 8 illustrates the exemplary distal embedding member connector in an unlocked configuration. As for the proximal embedding member connector, a locking screw (not shown) may bring the blocks 47 and 48 together until they contact one another to secure the distal embedding member 20 to the distal embedding member connector 22 and fix the position of the distal member connector 22 with respect to the distal bar 14. Distal embedding member connectors 22 may be positioned along the length of the uncurved portion of the distal bar 14 as shown in FIG. 1.

Figure 10:
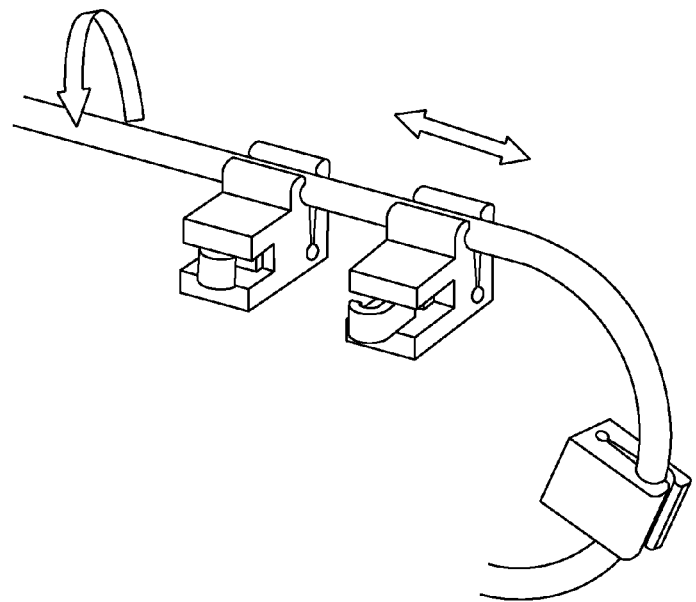
FIG. 10 illustrates connector motions along a distal bar.
Figure 11:
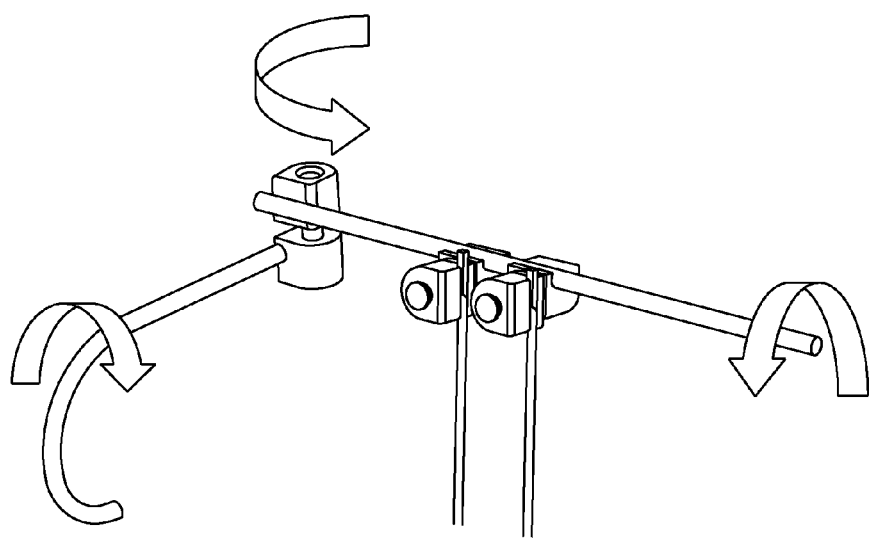
FIG. 11 illustrates various degrees of freedom in an embodiment of an external fixation system.

Distal embedding member connectors 22 may slide and/or rotate along and with respect to the distal bar (FIG. 10). These motions, taken with other possible adjustments (shown in FIG. 11), illustrate the various ways by which the distal bar position and orientation may be controlled.

The semicircular groove 44 and the through hole 46 may be connected by an angled cutout 44 as shown in FIG. 8. The angled cutout 44 or other similar shapes that have a decreasing width may facilitate clamping of the distal embedding member connector 22 by providing initial resistance to connection that abruptly gives way with a click to provide audible and tactile confirmation of correct positioning.

Some or all portions of the proximal and/or distal embedding member connectors may be made with radiolucent material such as carbon fiber.

Figure 12:
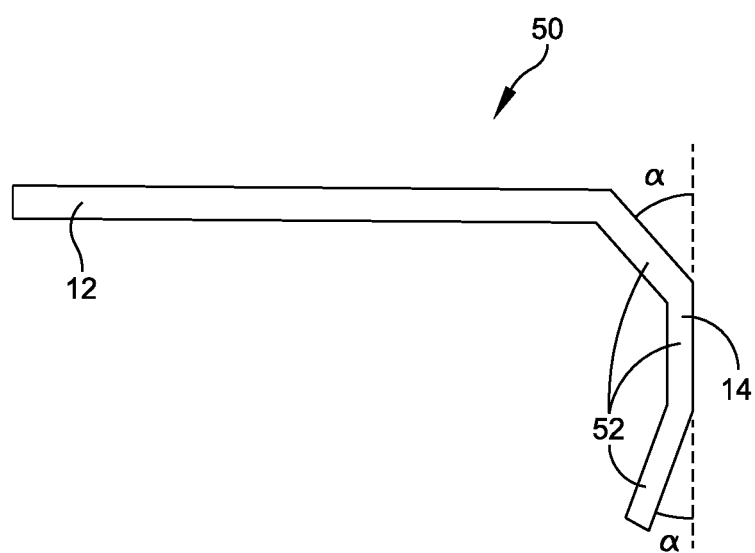
FIG. 12 shows and embodiment with a distal bar having multiple linear segments
Figure 23:
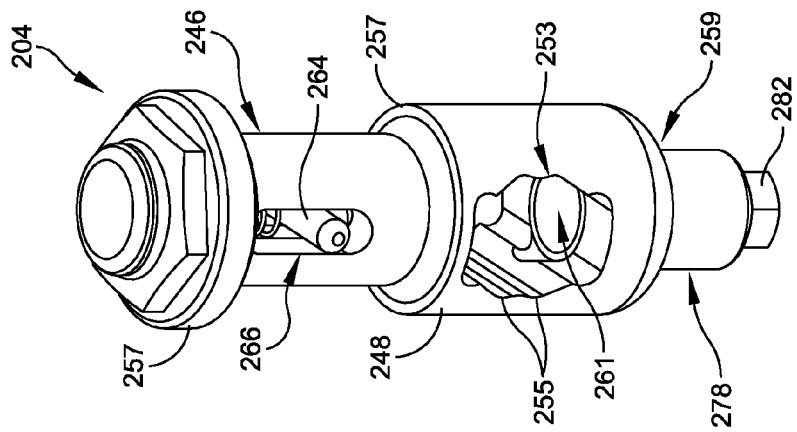
FIG. 23 is an isometric view of the improved connector illustrated in FIG. 19 with the jaws having been removed.

FIG. 12 shows a distal bar 50 for an external fixation system having a plurality of linear segments 52 bent at angles relative to one another. The distal bar 50 may have one, two, three, four, five, six, or more linear segments. Adjacent linear segments 52 may extend relative to one another at an angle α in the range of about 5 degrees to about 20 degrees, separately for each occurrence. The distal embedding member connectors 22 as shown in FIG. 1 may be used in this configuration to secure the distal embedding members 20 to the linear segments 52. In some embodiments, there may be a single linear segment 52 which may extend from the rest of the bar at a variety of angle. If that single linear segment extends at an angle of or about 90 degrees, then the bar is referred to herein as an "L-bar."

FIGS. 13-18 illustrate another embodiment of a connector 100 that includes first and second clamps 102-1, 102-2 (collectively referred to as "clamps 102") coupled together by a coupling assembly 104. The use of "-1," "-2," etc. in the description and/or in the figures identifies the existence of multiple like elements that have the same structure. Further, it is to be understood that reference "clamp 102" refers to all clamps "102-1" and "102-2." Clamps 102 include a first and second jaws 106 (e.g., jaws 106-1, 106-2), 108 (e.g., jaws 108-1, 108-2) that together define a channel 110 (e.g., channels 110-1, 110-2) for receiving and clamping onto a bar. Jaws 106 include a substantially circular body 112 (e.g., body 112-1, 112-2) having a substantially smooth mating side 114 (e.g., mating side 114-1, 114-2) disposed opposite an external side 116 (e.g., external side 116-1, 116-2) as best seen in FIG. 15. A hole 118 (e.g., hole 118-1, 118-2) extends from external side 116 to mating side 114 and includes an enlarged opening 120 (e.g., openings 120-1, 120-2) to define a shoulder 122 (e.g., shoulders 122-1, 122-2) shown in FIGS. 13 and 15. As shown in FIG. 17, in some embodiments, an internal hex 121 is provided within enlarged opening 120-1.

As best seen in FIG. 14, arm 124 (e.g., arms 124-1, 124-2) outwardly extends from jaw body 112 and includes a lip 126 (e.g., lips 126-1, 126-2) at its outer edge that that extends in a substantially perpendicular direction with respect to the direction in which arm 124 extends from jaw body 112. A tab 128 (e.g., tabs 128-1, 128-2) extends from external side 116 away from body 112. Although tab 128 is shown in FIG. 16 as being disposed on the opposite side of body 112 as arm 124 and having a substantially rectangular shape, tab 128 may be disposed at other locations on body 112 and have other shapes including, but not limited to, semi-circular, triangular, pentagonal, to name a few possible shapes.

Jaws 108 include a body 130 (e.g., body 130-1, 130-2) including a substantially smooth mating side 132 (e.g., side 132-1, 132-2) configured to abut mating side 114 of jaw 106 and a second mating side 134 (e.g., side 134-1, 134-2) disposed opposite mating side 132. In some embodiments, mating side 134 includes a plurality of grooves 136 (e.g., grooves 136-1, 136-2) configured to engage grooves of another jaw 108 to fix the relative angle between adjacent clamps 102 as described below. Body 130 defines a hole 138 (e.g., holes 138-1, 138-2) that extends from side 132 to side 134 as best seen in FIGS. 15 and 18.

Jaw 108 also includes an arm 140 (e.g., arms 140-1, 140-2) that extends outwardly from mating side 134 and includes a lip 142 (e.g., lip 142-1, 142-2) that extends in a substantially perpendicular direction with respect to the direction in which arm 140 extends from body 130. Body 130 defines a notch 144 (e.g., notch 144-1, 144-2) having a complementary shape to tab 128 of jaw 106. As best seen in FIG. 16, notch 144 may be disposed the opposite side of body 130 as arm 140 although one skilled in the art will understand that notch 144 may be disposed at other locations on body 130 and have other shapes that are not complementary to tab 128.

Coupling assembly 104 includes a bolt 146 having an at least partially threaded shaft 148 with an enlarged head 150 at a first end 152. Opposite end 154 defines a hole 156 sized and configured to receive a compression spring 158 therein as best seen in FIG. 15. At least a portion of bolt 146 includes a substantially smooth external surface 162.

A pin 164 is sized and configured to be received within slot 166 defined by threaded shaft 148 and reduced diameter region 160. A nut 168 includes an enlarged base 170 from which a engagement area 172 extends. Engagement area 172 may have a variety cross-sectional geometries for being engaged by a tool. Examples of such cross-sectional areas include, but are not limited to, triangular, rectangular, pentagonal, and hexagonal, to name a few possible cross-sectional shapes. Nut 168 also includes a threaded hole 174 configured to engage the threaded shaft 148 of bolt 146.

A plug 176 is configured to be received within hole 156 to trap and retain compression spring 158 within hole 156 and retaining nut 168. In some embodiments, plug 176 is threaded as is hole 156. In some embodiments, plug 176 is press fit or welded within hole 156.

Connector 100 is assembled by sliding a first jaw 106-1 onto bolt 146 such that enlarged opening 120-1 of hole 118-1 receives enlarged head 150 of bolt 146. Jaw 108-1 is then slid onto bolt 146 such that smooth mating side 132 abuts mating side 114 of jaw 106-1. Jaws 106-1 and 108-1 may be rotated around bolt 146 until tab 128-1 of jaw 106-1 is received within notch 144-1 of jaw 108-1 to ensure that arms 124-1 and 140-1 together define channel 110-1 of clamp 102-1 that is sized and configured to receive a bar or pin therein.

Second clamp 102-2 of connector 100 is assembled by sliding jaw 108-2 onto bolt 146 such that mating side 134-2 of jaw 108-2 abuts mating side 134-1 of jaw 108-1. Jaw 106-2 is slid onto bolt 146 such that tab 128-2 is aligned with notch 144-2 of jaw 108-2. With tab 128-2 disposed within notch 144-2, arm 124-2 is substantially aligned with arm 140-2, which together define channel 110-2.

Pin 164 is slid into slot 166 defined by bolt 146 and is received within enlarged opening 120-2 of jaw 106-2. Nut 168 is threaded onto bolt 146 by rotating nut 168 in a first direction (e.g., a clockwise direction) until enlarged base 170 contacts mating surface 116-2 of jaw 106-2. Compression spring 158 is inserted into hole 156 defined by bolt 146 and secured therein by inserting plug 176 into hole 156.

Figure 21:
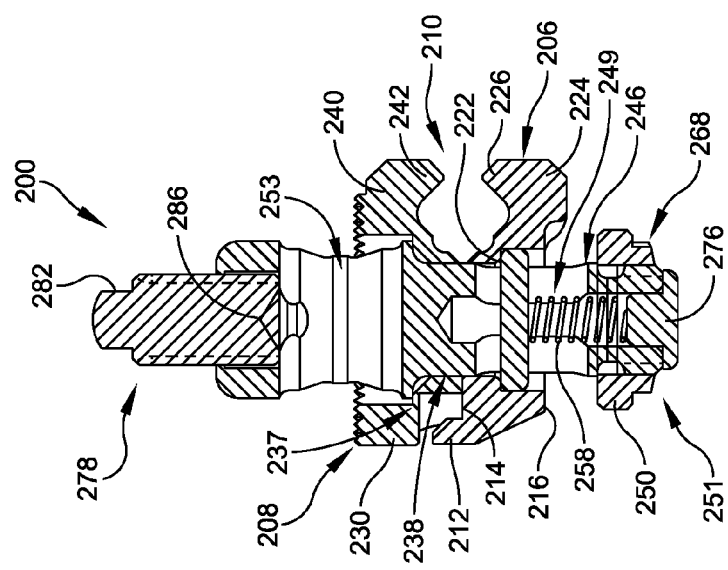
FIG. 21 is a sectional view of the improved connector illustrated in FIG. 19 taken along line A-A in FIG. 20.
Figure 19:
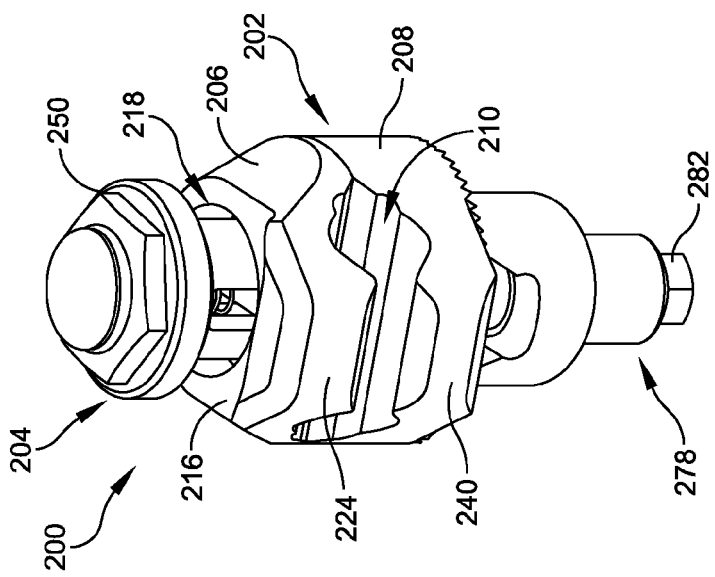
FIG. 19 is an isometric view of another example of an improved connector for providing external fixation.
Figure 22:
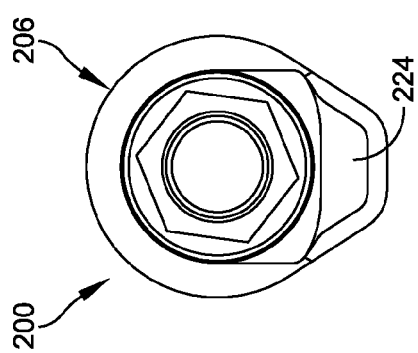
FIG. 22 is a top side view of the improved connector illustrated in FIG. 19.

FIGS. 19-24 illustrate another embodiment of a connector 200 in accordance with some embodiments. Connector 200 includes a clamp 202 includes a pair of jaws 206, 208 that are coupled together by a coupling assembly 204. Each jaw 206, 208 includes a respective arm 224, 240 that together define a channel 210. Jaw 206 has a circular body 212 including a smooth mating side 214 disposed on the opposite side of body 212 as external side 216 as best seen in FIGS. 19 and 21. Jaw 206 defines a hole 218 sized and configured to receive 246 of coupling assembly 204 therein. Hole 218 communicates with an enlarged opening 220 such that a shoulder 222 is formed.

Figure 20:
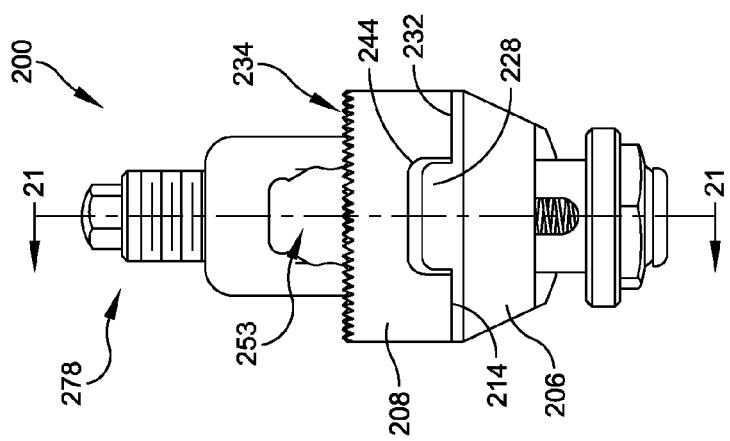
FIG. 20 is a side view of the improved connector illustrated in FIG. 19.
Figure 24:
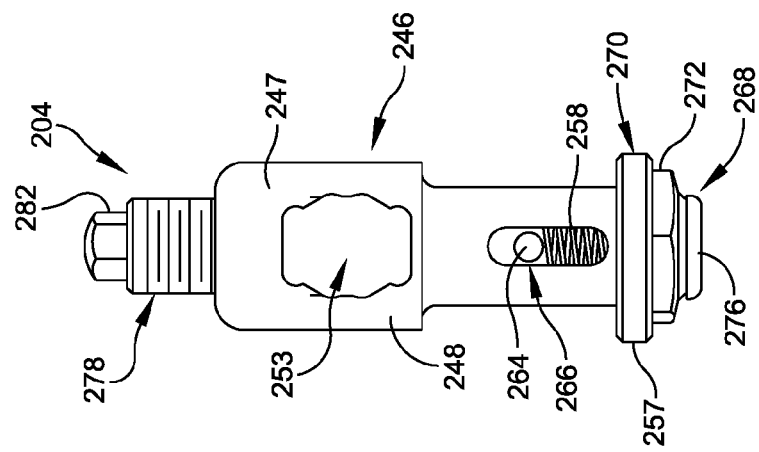
FIG. 24 is a side view of the improved connector illustrated in FIG. 19 with the jaws having been removed.

As best seen in FIG. 21, a lip 226 extends from the outer edge of arm 224 and is configured to grasp or otherwise engage a pin or bar of an external fixation device. Body 212 of jaw 206 includes an outwardly extending tab 228 as best seen in FIG. 20. Although tab 228 is shown in FIG. 20 as being disposed on the opposite side of body 212 as arm 224 and as having a substantially rectangular shape, tab 228 may be disposed at other locations on body 112 and have other shapes including, but not limited to, semi-circular, triangular, pentagonal, to name a few possible shapes.

Jaw 208 has a body 230 with a smooth mating side 232 (FIG. 20) that is configured to engage mating side 214 of jaw 206. A second mating side 234 of jaw 208 includes a plurality of grooves 236 for assisting in locking jaw 208 in a relative position of another jaw that includes a grooved mating surface. Body 230 of jaw 208 defines a hole 238 that extends from side 232 to side 234 and includes an outwardly extending arm 240. Arm 240 extends from mating side 234 and includes a lip 242 for assisting in the securement of a pin or a rod in channel 210.

As best seen in FIG. 20, a notch 244 having a complementary shape to tab 228 of jaw 206 is defined by body 230. In some embodiments, notch 244 is defined on the opposite side of body 230 as the side of the body 230 from which arm 240 extends; however, notch 244 may be located otherwise on body 244.

Coupling assembly 204 includes a bolt 246, a biasing member 258, such as a compression spring, and a pin 264.

Bolt 246 of coupling assembly 204 has an elongate body 248 defining a hole 249 at a first end 251 that is sized and configured to receive compression spring 258 therein. Biasing member 258 is sealed within hole 249 by a plug 276. A nut 268 includes an enlarged base 270 from which engagement area 272 extends. Engagement area 272 may have a variety cross-sectional geometries for being engaged by a tool such as, for example, a wrench. Nut 268 also includes a threaded hole 174 configured to engage the threaded shaft 248 of bolt 246.

Body 247 of bolt 246 defines a slot 253 (FIG. 24) along its length that has a geometry that is configured to engage a pin including a hexagonal cross section, such as pin 700 illustrated in FIGS. 38 and 39. In some embodiments, slot 253 includes a plurality of angled segments 255 for engaging flats defined by a pin as will be understood by one skilled in the art. Adjacent to slot 253 is a shoulder 257 that radially extends from body 247. End 259 of body 247 defines a threaded hole 261 that communicates with slot 253 and is sized and configured to receive a set screw 278 having a cup point 280 at one end (FIG. 21) and a hex engagement surface 282 at the opposite end.

Connector 200 is assembled by sliding jaw 208 over end 251 (FIG. 19) of bolt 246 such that shoulder 257 of bolt 246 (FIG. 24) contacts ledge 237 of hole 238 (FIG. 21), which acts as a stop. Jaw 206 is slid onto bolt 246 until mating side 214 of jaw 206 contacts mating side 232 of jaw 208 and tab 228 is received within notch 244. Pin 264 is inserted into slot 266 (FIGS. 23, 24), and compression spring 258 is inserted into hole 249 such that spring 258 contacts pin 264. Plug 276 is press-fit (or threaded) into hole 249, and set screw 278 is threaded into hole 261. Nut 268 is threaded onto end 251 of bolt 245 until enlarged base 270 contacts external side 216.

FIGS. 25-27 illustrate another example of a coupling assembly 300. Coupling assembly 300 includes a pin engaging segment 302 and a bar engaging segment 304. Pin engaging segment 302 includes a base 306 from which an elongate shaft 308 extends. Base 306 may have a substantially circular cross-sectional area and define a hole 310 that extends through base 306 in a direction that is approximately perpendicular to the longitudinal axis defined by shaft 308. Hole 310 is sized and configured to receive a pin therein. Base 306 defines a threaded hole 312 (FIG. 27) that extends in a substantially parallel direction to the longitudinal axis defined by shaft 308. Shaft 308 has a substantially smooth exterior surface 314 and defines a circumferential groove 316 adjacent to end 318. Groove 316 is configured to receive clamp 320 for retaining bar engaging segment 304 disposed on shaft 308.

Bar engaging segment 304 includes a body 322 that defines hole/slot 324 having a diameter that is sized and configured to slidably receive shaft 308. A bar-receiving hole 326 extends through body 322 in a substantially perpendicular widthwise direction to the direction in which hole/slot 324 extends. Hole 326 includes one or more scallops 328 disposed around the periphery 330 of hole 326. A hole 330 extends through body 322 substantially parallel to bar-receiving hole 326 and at least partially intersects hole 324. A cork 332 fabricated from an elastomeric material, such as silicone, is received within hole 326 and extends into hole 324 as best seen in FIG. 27. Body 322 also defines a threaded hole 340 that extends perpendicular to and intersects hole 324.

Coupling assembly 300 also includes a pair of set screws 336-1, 336-2 (collectively referred to as "set screws 336") each having a threaded body 338 and an engagement section 340. In some embodiments, engagement section 340 has a hexagonal cross-sectional geometry although one skilled in the art will understand that engagement section 340 may have other cross-sectional geometries. Bottom end 342 of set screws 336 may define a depression 344 such that set screws 336 have a cup-shape as best seen in FIG. 27.

Coupling assembly 300 is assembled by press-fitting elastomeric cork 332 into hole 331 of body 322. Shaft 308 is slid into hole 324 and then clamp 320 is secured within circumferential groove 316. Set screws 336 are threaded into threaded holes 312 and 340.

FIGS. 28-30 illustrate another example of a coupling assembly 400 that is similar to coupling assembly 300. Like elements of coupling assembly 400 have the same reference numerals as the elements of coupling assembly 300 increased by "100", and detailed description of these like elements are not provided. As best seen in FIGS. 28 and 30, body 422 of bar engaging segment 404 includes an opening 446 that communicates with hole 426 such that bar engagement segment 404 may be clipped or snapped onto a bar instead of being slipped or slid onto a bar like coupling assembly 300.

Figure 34:
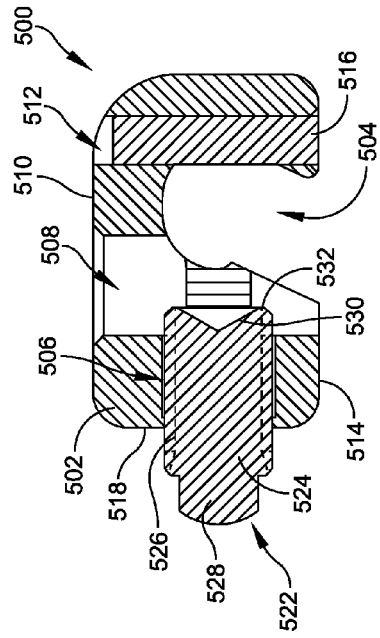
FIG. 34 is a sectional view of the improved connector illustrated in FIG. 31 taken along line A-A in FIG. 33.
Figure 31:
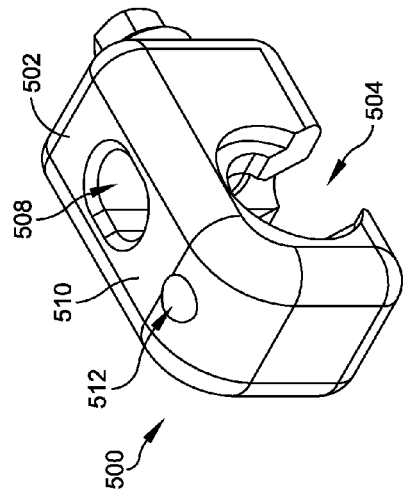
FIG. 31 is an isometric view of another example of an improved connector for providing external fixation.
Figure 33:
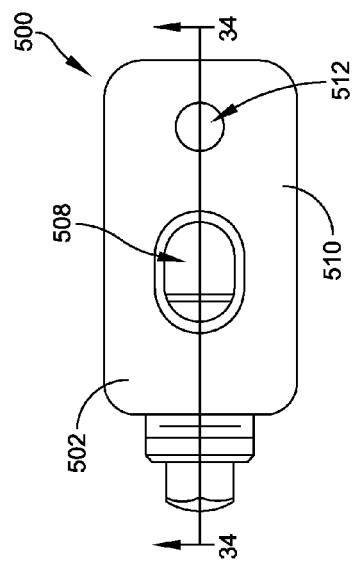
FIG. 33 is a top side view of the improved connector illustrated in FIG. 31.
Figure 32:
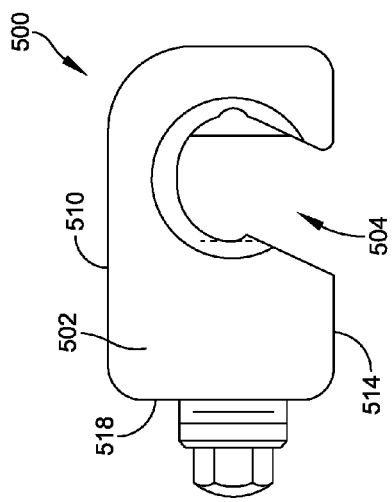
FIG. 32 is a side view of the improved connector illustrated in FIG. 31.

FIGS. 31-34 illustrates another example of a connector 500 for coupling a pin to a bar including a body 502 having a substantially rectangular shape defining an opening 504 that communicates with a hole 512 (best seen in FIGS. 34), which extends in a widthwise direction through body 502. A slot 508 extends from a top side 510 of body and at least partially intersects opening 504 and a threaded hole 506 as best seen in FIG. 34. In some embodiments, slot 508 has an oblong oval shape although those skilled in the art will understand that the slot 508 may have other geometries. Hole 512 is sized and configured to receive a cork 516 in a press-fit engagement. Cork 516 may be fabricated from an elastomeric material such as, for example, silicone.

Side wall 518 defines threaded hole 506 that extends in a longitudinal direction of body 502 and intersects hole 508 and 504 as noted above. Hole 506 is sized and configured to receive set screw 522 having an elongate body 524 having threads 526 disposed thereon and a head 528 having a hexagonal cross-sectional geometry. Set screw 522 may be a cup-point set screw defining a depression 530 at its leading end 532 for enhancing the engagement when contacting a pin.

FIGS. 35-37 illustrate another example of a connector 600 for an external fixation system in accordance with some embodiments. Connector 600 comprises a base 602 including a hollow shaft 604 extending a first direction and a jaw 606 extending in a second direction that diverges from the first direction. Shaft 604 has a reduced diameter compared to jaw 606 of base 602 such that a shoulder 608 is formed at the interface of shaft 604 and jaw 606. Base 602 defines a channel 610 that extends in a direction parallel to jaw 606. In some embodiments, channel 610 extends entirely through base 602, although in some embodiments channel 610 does not extend entirely through base 602. Channel 610 is sized and configured to receive a hexagonally shaped pin, such as pin 700 illustrated in FIGS. 38 and 39.

Base 602 defines a hole 612 that extends transversely across jaw 606 such that a portion of hole 612 communicates with channel 610 as best seen in FIG. 612. In some embodiments, upper surface 614 of jaw 606 includes a plurality of teeth 616 or other texturing to increase the friction of jaw 606.

Connector 600 also includes a sliding jaw 618 that defines a central passage 620 that is sized and configured to receive and slide along shaft 604. An arm 622 outwardly extends from sliding jaw 618 and defines a recessed area 624. The combination of upper surface 614 of jaw 606 and arm 622 define a channel 626 that is sized and configured to receive a pin and/or bar of an external fixation system. Recessed area 624 can include scalloping 628 as best seen in FIG. 37. Sliding jaw 618 also defines an enlarged recessed area 630 that is concentric with central passage 620. This enlarged recessed area 630 is configured to provide an abutment for pin 632 that is received within slot 634 defined by shaft 604. Pin is biased by a biasing member 636, which is illustrated in FIG. 37 as compression spring.

A threaded nut 638 is configured to threadably engage the threaded portion 640 of shaft 604. Nut 638 includes an outwardly extending shoulder 642 and an engagement portion 644. Biasing member 636 is retained within the central chamber of hollow shaft 604 by a plug 646, which may be press-fit, threaded, or welded into the chamber. An elastomeric plug (not shown) may be received within hole 612 for frictionally engaging a pin received within channel 610.

For example, elastomeric plug may engage hexagonal area 702 of pin or bar 700 illustrated in FIGS. 38 and 39. As best seen in FIG. 38, pin 700 can include a cylindrical area 704 that transitions to a hexagonal area 702. Although not shown in FIGS. 38 and 39, pin or bar 700 can include a threaded end.

Figure 40:
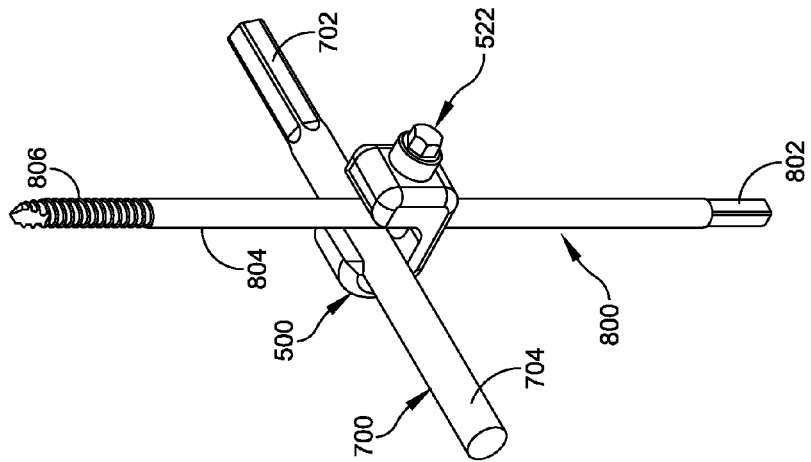
FIG. 40 is an isometric view of an example of a connector coupling together a rod and a screw in accordance with some embodiments.
Figure 41:
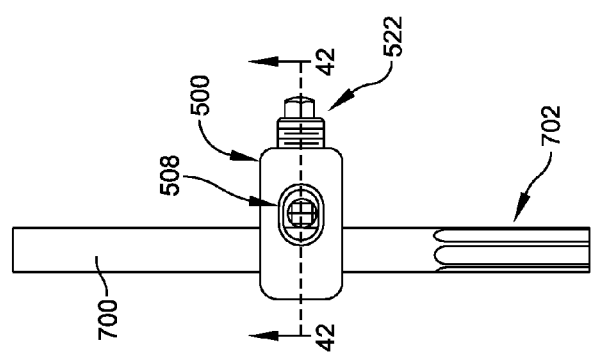
FIG. 41 is a side view of the connector coupling together a rod and a screw illustrated in FIG. 40.
Figure 42:
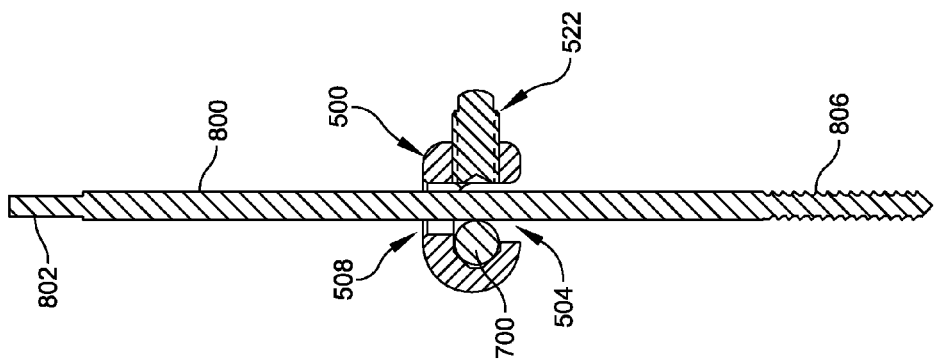
FIG. 42 is a sectional view of the connector coupling together a rod and a screw taken along line A-A in FIG. 41.
Figure 48:
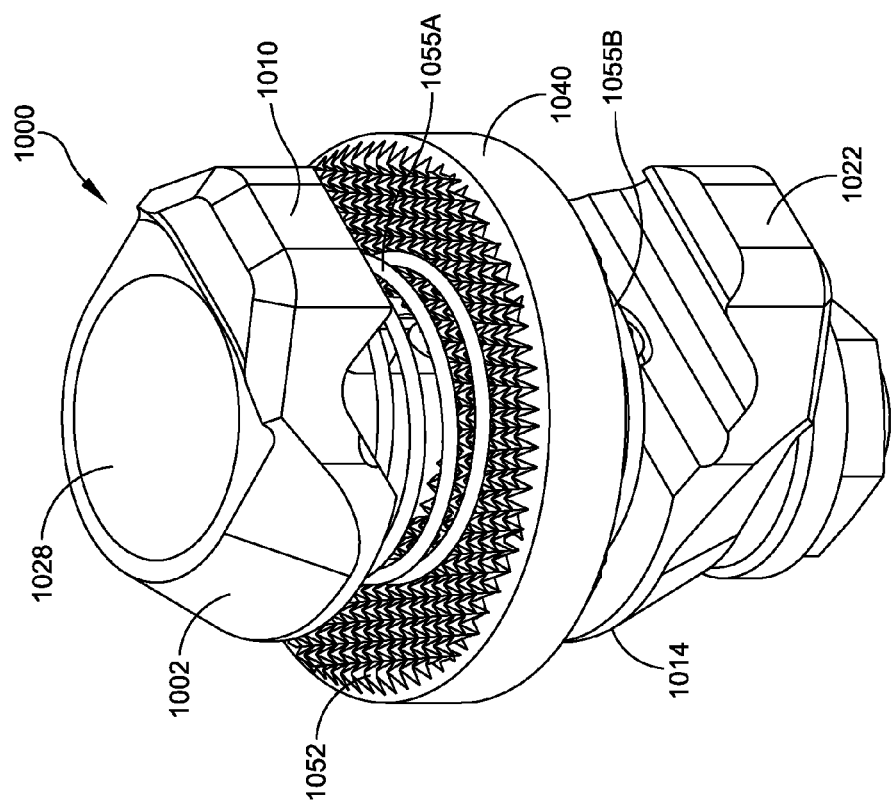
FIG. 48 is an isometric view of another example of a connector in accordance with some embodiments.

FIGS. 40-42 illustrate an example of a connector 500 being coupled to a bar 700 and a pin 700. Referring first to FIG. 40, rod 700 is received opening 504 of connector 500 and a pin 800 is received within slot 508 such that pin 800 extends in a direction that is perpendicular to the direction in which bar 700 extends. Pin 800 includes an engagement end 802, which is illustrated as having a square cross-sectional geometry, that is disposed opposite threaded end 806 with a smooth surface 804 disposed between the opposite ends 802, 806. Although engagement end 802 is illustrated as having a square cross-sectional geometry, engagement end 802 can have other cross-sectional geometries including, but not limited to, a hexagonal geometry. Set screw 522 is used to releasably lock connector 500 to rod 700 and pin 800.

FIGS. 43-47 illustrate one example of a wrench 900 that can be used to fasten the connectors 100, 200, 300, 400, 500, 600 described above to rods 700 and/or pins 800. Referring first to FIG. 43, wrench includes an elongate body 902 including a first end 904 and an opposed second end 906. In some embodiments, body 902 includes a textured surface 908 for improving manipulation of wrench 900 by a user. As best seen in FIGS. 44 and 45, end 904 includes a pair of opposed flats 910, 912 and defines a hexagonal channel 914 therethrough. Channel 914 is sized and configured to engage the engagement sections 340, 440, 528 of set screws 336, 436, 522.

End 906 defines a blind hole 916 that can include a square or hexagonal shape for engaging set screws 336, 436, 522 and/or ends of rods 700 and/or pins 800. As best seen in FIG. 47, blind hole inwardly ends from end 906 in a lengthwise direction.

FIGS. 49-52 illustrate another example of a connector 1000. Connector 1000 includes a first jaw 1002 defining a central passageway 1004 that extends entirely through jaw 1002. An enlarged area 1006 is concentric with passageway 1004 and provides a shoulder 1008. Jaw 1002 also includes an arm 1010 that outwardly extends and defines a recessed area 1012. A second jaw 1014 also defines a central passageway 1016 and a pair of enlarged areas 1018 and 1020. An arm 1022 outwardly extends from jaw 1014 and defines a recessed area 1024.

A partially threaded bolt 1026 includes a head 1028 at one end 1030 and defines an opening 1032 at an opposite end 1034 that extends to head 1028. Bolt 1026 defines an elongated slot 1036 that extends between first end 1030 and second end 1034. Slot 1036 intersects opening 1032 over a majority of the length of opening 1032. Bolt 1026 also includes threads 1038 along a portion of its length on its exterior surface adjacent end 1034.

A floating circular jaw 1040 defines a central hole 1042 that is sized and configured to slidably receive bolt 1026 therein. In some embodiments, circular jaw 1040 define notches 1044, 1046 in its upper surface 1048 and its lower surface 1050, respectively. In some embodiments, the upper surface 1048 and lower surface 1050 include teeth 1052 or other textured surface for increasing the friction of upper and lower surfaces 1048, 1050. Floating jaw 1040 defines first and second channels 1054, 1056 with jaws 1002 and 1014.

Figure 50:
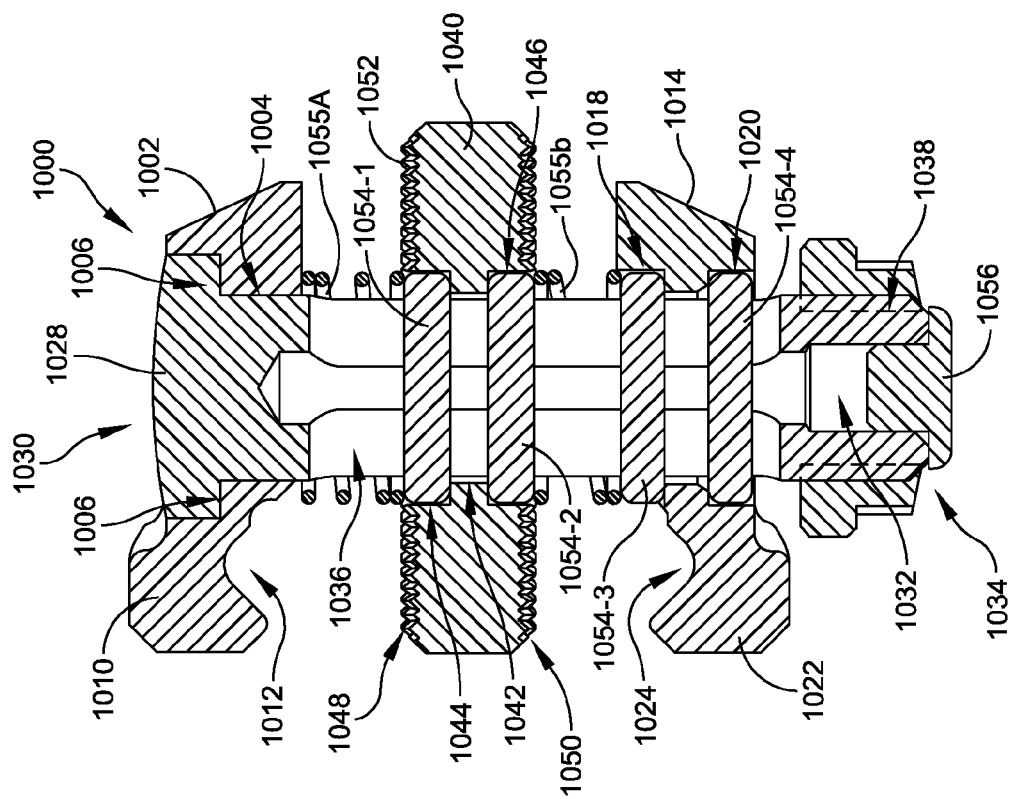
FIG. 50 is a sectional view of the connector illustrated in FIG. 49 taken along line A-A in FIG. 49.
Figure 49:
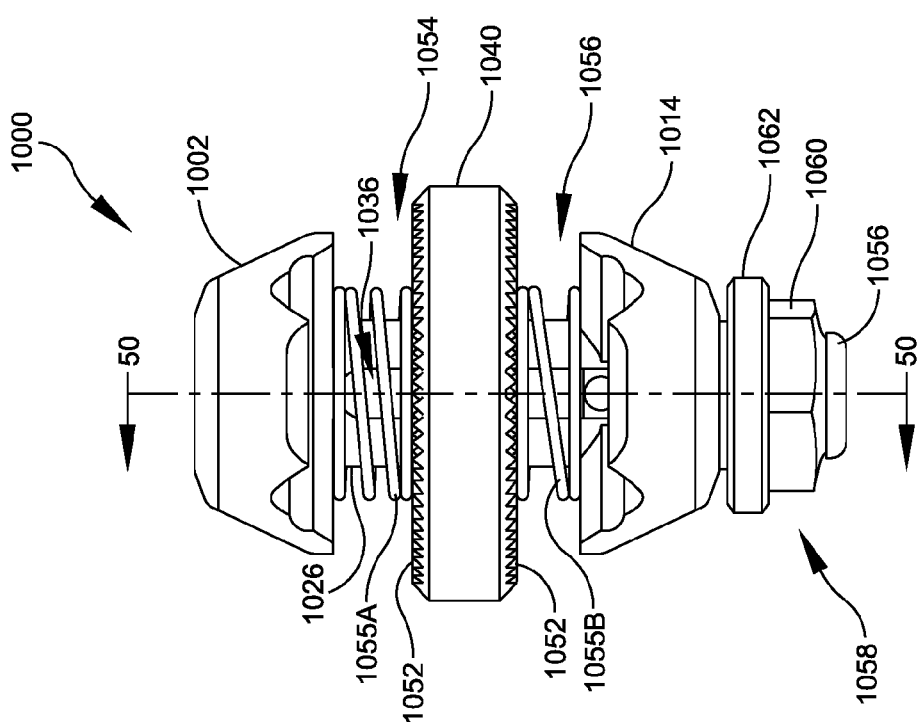
FIG. 49 is a side view of the connector illustrated in FIG. 48.
Figure 51:
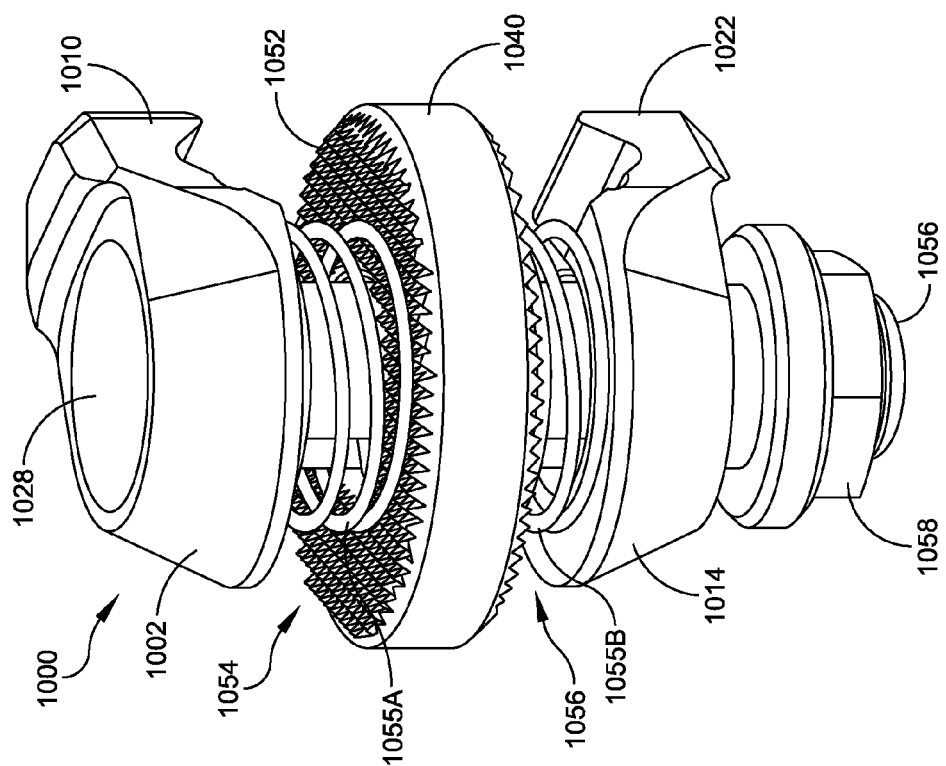
FIG. 51 is another isometric view of the connector illustrated in FIG. 48.

Connector 1000 includes a plurality of pins 1054-1, 1054-2, 1054-3, 1054-4 and biasing members 1055a and 1055b to distance circular jaw 1040 from jaws 1002 and 1014. For example and as best seen in FIG. 50, pins 1054-1, 1054-2 are received within notches 1044, 1046, respectively, and pins 1054-3, 1054-4 are received within enlarged areas 1018, 1020, respectively. A first biasing member 1055a is disposed within central passageway 1004 and is disposed between jaw 1002 and floating circular jaw 1040 such that the biasing member contacts pin 1054-1. The second biasing member 1055b is disposed within central passageway 1004 between jaw 1014 and end cap 1056 that secures biasing members within central passageway 1004. A locking nut 1058 is configured to engage threads 1038 of bolt 1026. Locking nut 1058 includes an engagement surface 1060 and an enlarged diameter section 1062.

In some embodiments, the biasing members have an equal spring coefficient such that they provide an equal and opposite force on floating jaw 1040. In some embodiments, biasing members have unequal spring coefficients and the passageway 1004 in which biasing members are disposed has a diameter that is smaller than the diameter of the pins 1054. When bars or pins are received within channels 1054 and 1056 in the desired position, locking nut 1058 is turned to urge jaw 1014 towards jaws 1040, 1002 to lock the pins and/or rods within channels 1054, 1056.

As discussed previously, external fixation systems described herein may be used to provide non-bridging fixation for fractures of the distal radius. They may also be used to provide spanning fixation and/or distraction across a distal radius fracture and/or across one or more bones of the carpus. The disclosed external fixation systems may also be used in treating fractures of other bones, such as metacarpals, phalanges in hands or feet, ulna, humerus, clavicle, scapula, the bony pelvis, femur, tibia, fibula, bones of the ankle, and/or metatarsals.

Although the disclosed devices, systems, and methods have been described in terms of exemplary embodiments, they are not limited thereto. Rather, the appended claims should be construed broadly, to include other variants and embodiments of the devices, systems, and methods, which may be made by those skilled in the art without departing from the scope and range of equivalents of the devices, systems, and methods.

What is claimed is:

1. An orthopedic fixation device, comprising:
   first and second jaws each including respective arms;
   a floating circular jaw disposed between the first and second jaws and defining first and second channels with the first and second jaws, respectively, the first and second channels each being configured to receive one of an embedding member or a bar of an external fixation system;
   a plurality of pins and biasing members configured to distance the circular jaw from the first and second jaws; and
   a locking assembly at least partially received within apertures defined by the first, second, and circular jaws and being configured to lock the first, second, and circular jaws;
   a first one of the plurality of biasing members is disposed within a central passageway defined by a bolt of the locking assembly and is disposed between the first jaw and the circular jaw such that the first biasing member contacts a first pin; and
   a second one of the plurality of biasing members is disposed within the central passageway between the second jaw and an end cap that secures the first and second biasing members within the central passageway, the second biasing member configured to bias the circular jaw away from the second jaw.

2. The device of claim 1, wherein the circular jaw defines notches in its upper surface and its lower surface, respectively.

3. The device of claim 1, wherein the upper surface and lower surface of the circular jaw include teeth or other textured surface for increasing the friction of the upper and lower surfaces.

4. The device of claim 1, wherein the biasing members have equal spring coefficients such that they provide an equal and opposite force on the circular jaw.

5. The device of claim 1 wherein the first and second biasing members have equal spring coefficients such that they provide an equal and opposite force on the circular jaw.

6. The device of claim 5, wherein the circular jaw defines notches in its upper surface and its lower surface, respectively.

7. The device of claim 5, wherein the upper surface and lower surface of the circular jaw include teeth or other textured surface for increasing the friction of the upper and lower surfaces.

8. The device of claim 1, wherein the locking assembly comprises:
   a bolt that defines an elongated slot that extends between a top end and a bottom end of the bolt, the bottom end of the bolt defining an opening that extends to a head of the bolt and intersects the slot over a majority of a length of the opening, the bolt including threads disposed along a portion of the bolt's length on an exterior surface of the bolt; and
   a locking nut configured to engage the threads of the bolt.

9. The device of claim 8, wherein the biasing members have an equal spring coefficient such that they provide an equal and opposite force on the circular jaw.

10. An external fixation system comprising:
    at least one bar and at least one embedding member attachable to the bar and sized and shaped for embedding in bone; and
    at least one embedding member connector configured to be coupled to the bar, the at least one embedding member connector comprising:
    first and second jaws each including respective arms;
    a floating circular jaw disposed between the first and second jaws and defining first and second channels with the first and second jaws, respectively, the first and second channels each being configured to receive at least one of the at least one bar and the at least one embedding member of the external fixation system; a plurality of pins and biasing members configured to distance the circular jaw from the first and second jaws; and a locking assembly at least partially received within apertures defined by the first, second, and circular jaws and being configured to lock the first, second, and circular jaws;

a first one of the plurality of biasing members is disposed within a central passageway defined by a bolt of the locking assembly and is disposed between the first jaw and the circular jaw such that the first biasing member contacts a first pin; and a second one of the plurality of biasing member is disposed within the central passageway between the second jaw and an end cap that secures the first and second biasing members within the central passageway, the second biasing member configured to bias the circular jaw away from the second jaw.

11. The system of claim 10, wherein the circular jaw defines notches in its upper surface and its lower surface, respectively.

12. The system of claim 10, wherein the upper surface and lower surface of the circular jaw include teeth or other textured surface for increasing the friction of the upper and lower surfaces.

13. The system of claim 10 wherein the biasing members have equal spring coefficients such that they provide an equal and opposite force on the circular jaw.

14. The system of claim 10 wherein the first and second biasing members have equal spring coefficients such that they provide an equal and opposite force on the circular jaw.

15. The system of claim 10, wherein the looking assembly comprises:

a bolt that defines an elongated slot that extends between a top end and a bottom end of the bolt, the bottom end of the bolt defining an opening that extends to the head of the bolt and intersects the slot over a majority of a length of the opening, the bolt including threads along a portion of the bolt's length on an exterior surface of the bolt; and a locking nut configured to engage the threads of the bolt.

16. A method of assembling an orthopedic fixation device, the method comprising:

sliding a first jaw onto a bolt;

sliding a floating circular jaw onto said bolt;

sliding a second jaw onto the bolt;

inserting a plurality of pins and biasing members into an opening defined by the bolt to distance the circular jaw from the first and second jaws; and affixing a locking nut onto a threaded portion of the bolt to secure the plurality of pins and biasing members within said opening, wherein the circular jaw defines first and second channels with the first and second jaws, respectively, that are configured to receive at least one of an embedding member or a bar therein;

wherein the opening defined by the bolt extends to a head of the bolt and intersects an elongated slot that extends between a top end and a bottom end of the bolt.

17. A method of assembling an orthopedic fixation device, the method comprising:

sliding a first jaw onto a bolt;

sliding a floating circular jaw onto said bolt;

sliding a second jaw onto the bolt;

inserting a plurality of pins and biasing members into an opening defined by the bolt to distance the circular jaw from the first and second jaws; and affixing a locking nut onto a threaded portion of the bolt to secure the plurality of pins and biasing members within said opening, wherein the circular jaw defines first and second channels with the first and second jaws, respectively, that are configured to receive at least one of an embedding member or a bar therein; wherein inserting the pins comprises inserting the pins into respective notches on the upper surface and lower surface of the circular jaw.

\* \* \* \* \*